(12) United States Patent
Davenport et al.

(10) Patent No.: US 10,702,393 B2
(45) Date of Patent: Jul. 7, 2020

(54) EXPANDABLE INTERVERTEBRAL IMPLANT

(71) Applicant: GLOBUS MEDICAL, INC., Audubon, PA (US)

(72) Inventors: Daniel Davenport, Collegeville, PA (US); Chad Glerum, Pennsburg, PA (US); Duncan Sibson, Malvern, PA (US)

(73) Assignee: Globus Medical Inc., Audubon, PA (US)

( * ) Notice: Subject to any disclaimer, the term of this patent is extended or adjusted under 35 U.S.C. 154(b) by 0 days.

(21) Appl. No.: 15/802,688

(22) Filed: Nov. 3, 2017

(65) Prior Publication Data

US 2018/0055652 A1    Mar. 1, 2018

Related U.S. Application Data

(63) Continuation of application No. 15/291,108, filed on Oct. 12, 2016, now Pat. No. 9,833,336, which is a
(Continued)

(51) Int. Cl.
*A61F 2/46* (2006.01)
*A61F 2/44* (2006.01)
(Continued)

(52) U.S. Cl.
CPC ............ *A61F 2/447* (2013.01); *A61F 2/442* (2013.01); *A61F 2/4455* (2013.01);
(Continued)

(58) Field of Classification Search
CPC .. A61F 2/442; A61F 2/4425; A61F 2002/443; A61F 2/4455; A61F 2/446;
(Continued)

(56) References Cited

U.S. PATENT DOCUMENTS

| 4,349,921 A | 9/1982 | Kuntz |
| 4,599,086 A | 7/1986 | Doty |

(Continued)

FOREIGN PATENT DOCUMENTS

| CA | 2088066 A1 | 1/1992 |
| DE | 4012622 C1 | 7/1991 |

(Continued)

OTHER PUBLICATIONS

U.S. Appl. No. 60/777,663, filed Feb. 27, 2006, Messerli.
(Continued)

*Primary Examiner* — Julianna N Harvey
*Assistant Examiner* — Christina Negrellirodriguez

(57) ABSTRACT

An implant for therapeutically separating bones of a joint has two endplates each having an opening through the endplate, and at least one ramped surface on a side opposite a bone engaging side. A frame is slideably connected to the endplates to enable the endplates to move relative to each other at an angle with respect to the longitudinal axis of the implant, in sliding connection with the frame. An actuator screw is rotatably connected to the frame. A carriage forms an open area aligned with the openings in the endplates. The openings in the endplates pass through the carriage to form an unimpeded passage from bone to bone of the joint. The carriage has ramps which mate with the ramped surfaces of the endplates, wherein when the carriage is moved by rotation of the actuator screw, the endplates move closer or farther apart.

18 Claims, 16 Drawing Sheets

Related U.S. Application Data continuation of application No. 14/676,323, filed on Apr. 1, 2015, now Pat. No. 9,486,325, which is a continuation of application No. 13/836,005, filed on Mar. 15, 2013, now Pat. No. 9,149,367.

(51) Int. Cl.
*A61B 17/80* (2006.01)
*A61F 2/30* (2006.01)

(52) U.S. Cl.
CPC ......... *A61B 17/8042* (2013.01); *A61F 2/4684* (2013.01); *A61F 2002/3008* (2013.01); *A61F 2002/30062* (2013.01); *A61F 2002/30181* (2013.01); *A61F 2002/30266* (2013.01); *A61F 2002/30387* (2013.01); *A61F 2002/30405* (2013.01); *A61F 2002/30448* (2013.01); *A61F 2002/30476* (2013.01); *A61F 2002/30556* (2013.01); *A61F 2002/30579* (2013.01); *A61F 2002/30593* (2013.01); *A61F 2002/30607* (2013.01); *A61F 2002/30616* (2013.01); *A61F 2002/30677* (2013.01); *A61F 2002/30787* (2013.01); *A61F 2310/00023* (2013.01); *A61F 2310/00029* (2013.01); *A61F 2310/00359* (2013.01)

(58) Field of Classification Search
CPC .......... A61F 2/4465; A61F 2/447; A61F 2/46; A61F 2002/4475
USPC ...................... 606/246–249; 623/17.11–17.16
See application file for complete search history.

(56) References Cited

U.S. PATENT DOCUMENTS

| | | |
|---|---|---|
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,397,364 A | 3/1995 | Kozak et al. |
| 5,458,641 A | 10/1995 | Jiminez |
| 5,522,899 A | 6/1996 | Michelson |
| 5,534,030 A | 7/1996 | Navarro et al. |
| 5,549,612 A | 8/1996 | Yapp et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 5,861,041 A | 1/1999 | Tienboon |
| 5,888,223 A | 3/1999 | Bray, Jr. |
| 6,039,761 A | 3/2000 | Li et al. |
| 6,045,579 A | 4/2000 | Hochschuler et al. |
| 6,066,175 A | 5/2000 | Henderson et al. |
| 6,080,193 A | 6/2000 | Hochschuler et al. |
| 6,099,531 A | 8/2000 | Bonutti |
| 6,102,950 A | 8/2000 | Vaccaro |
| 6,126,689 A | 10/2000 | Brett |
| 6,156,037 A | 12/2000 | LeHuec et al. |
| 6,176,882 B1 | 1/2001 | Biedermann et al. |
| 6,200,347 B1 | 3/2001 | Anderson et al. |
| 6,206,922 B1 | 3/2001 | Zdeblick et al. |
| 6,231,610 B1 | 5/2001 | Geisler |
| 6,258,089 B1 | 7/2001 | Campbell et al. |
| 6,258,125 B1 | 7/2001 | Paul et al. |
| 6,383,186 B1 | 5/2002 | Michelson |
| 6,432,106 B1 | 8/2002 | Fraser |
| 6,482,233 B1 | 11/2002 | Aebi |
| 6,540,785 B1 | 4/2003 | Gill et al. |
| 6,558,423 B1 | 5/2003 | Michelson |
| 6,558,424 B2 | 5/2003 | Thalgott |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,889 B1 | 12/2003 | Commarmond |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,740,118 B2 | 5/2004 | Eisermann et al. |
| 6,752,832 B2 | 6/2004 | Ulrich |
| 6,827,740 B1 | 12/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 6,899,735 B2 | 5/2005 | Coates et al. |
| 6,972,019 B2 | 12/2005 | Michelson |
| 7,001,432 B2 | 2/2006 | Keller et al. |
| 7,018,415 B1 | 3/2006 | McKay |
| 7,025,787 B2 | 4/2006 | Bryan et al. |
| 7,070,598 B2 | 7/2006 | Lim et al. |
| 7,137,997 B2 | 11/2006 | Paul |
| 7,147,665 B1 | 12/2006 | Bryan et al. |
| 7,153,325 B2 | 12/2006 | Kim et al. |
| 7,172,627 B2 | 2/2007 | Fiere et al. |
| 7,204,853 B2 | 4/2007 | Gordon |
| 7,217,291 B2 | 5/2007 | Zucherman et al. |
| 7,232,464 B2 | 6/2007 | Mathieu et al. |
| 7,276,082 B2 | 10/2007 | Zdeblick et al. |
| 7,282,063 B2 | 10/2007 | Cohen et al. |
| 7,309,357 B2 | 12/2007 | Kim |
| 7,316,714 B2 | 1/2008 | Gordon |
| 7,320,708 B1 | 1/2008 | Bernstein |
| 7,473,276 B2 | 1/2009 | Aebi et al. |
| 7,547,325 B2 | 6/2009 | Biedermann et al. |
| 7,618,456 B2 | 11/2009 | Mathieu et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,771,475 B2 | 8/2010 | Michelson |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,846,207 B2 | 12/2010 | Lechmann et al. |
| 7,862,616 B2 | 1/2011 | Lechmann et al. |
| 7,875,076 B2 | 1/2011 | Mathieu et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 8,100,976 B2 | 1/2012 | Bray et al. |
| 8,123,810 B2 | 2/2012 | Gordon |
| 8,343,222 B2 | 1/2013 | Cope |
| 8,647,386 B2 | 2/2014 | Gordon |
| 8,709,086 B2 * | 4/2014 | Glerum .................. A61F 2/447 623/17.16 |
| 2002/0010511 A1 | 1/2002 | Michelson |
| 2002/0016595 A1 | 2/2002 | Michelson |
| 2002/0045945 A1 | 4/2002 | Liu |
| 2002/0068976 A1 | 6/2002 | Jackson |
| 2003/0045939 A1 | 3/2003 | Casutt |
| 2003/0105528 A1 | 6/2003 | Shimp et al. |
| 2003/0125739 A1 | 7/2003 | Bagga et al. |
| 2003/0167091 A1 | 9/2003 | Scharf |
| 2004/0049271 A1 | 3/2004 | Biedermann |
| 2004/0054412 A1 | 3/2004 | Gerbec et al. |
| 2004/0078078 A1 | 4/2004 | Shepard |
| 2004/0143270 A1 | 7/2004 | Zucherman et al. |
| 2004/0143332 A1 | 7/2004 | Krueger et al. |
| 2004/0153065 A1 | 8/2004 | Lim |
| 2004/0176853 A1 | 9/2004 | Sennett et al. |
| 2005/0021041 A1 | 1/2005 | Michelson |

(56) References Cited

U.S. PATENT DOCUMENTS

| | | |
|---|---|---|
| 2005/0021145 A1 | 1/2005 | de Villiers et al. |
| 2005/0033432 A1 | 2/2005 | Gordon |
| 2005/0055098 A1 | 3/2005 | Zdeblick et al. |
| 2005/0065607 A1 | 3/2005 | Gross |
| 2005/0149188 A1 | 7/2005 | Cook |
| 2005/0149192 A1 | 7/2005 | Zucherman et al. |
| 2005/0149193 A1 | 7/2005 | Zucherman et al. |
| 2005/0159819 A1 | 7/2005 | McCormack et al. |
| 2005/0171541 A1 | 8/2005 | Boehm |
| 2005/0171607 A1 | 8/2005 | Michelson |
| 2005/0177236 A1 | 8/2005 | Mathieu et al. |
| 2005/0187625 A1 | 8/2005 | Wolek et al. |
| 2005/0240267 A1 | 10/2005 | Randall et al. |
| 2005/0240271 A1 | 10/2005 | Zubok et al. |
| 2005/0251258 A1 | 11/2005 | Jackson |
| 2005/0256574 A1 | 11/2005 | Paul et al. |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0058878 A1 | 3/2006 | Michelson |
| 2006/0085071 A1 | 4/2006 | Lechmann et al. |
| 2006/0122701 A1 | 6/2006 | Kister |
| 2006/0129240 A1 | 6/2006 | Lessar et al. |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0217809 A1 | 9/2006 | Albert et al. |
| 2006/0229729 A1 | 10/2006 | Gordon |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0088441 A1 | 4/2007 | Duggal et al. |
| 2007/0123987 A1 | 5/2007 | Bernstein |
| 2007/0135923 A1 | 6/2007 | Peterman et al. |
| 2007/0162130 A1 | 7/2007 | Rashbaum et al. |
| 2007/0168032 A1 | 7/2007 | Muhanna et al. |
| 2007/0191951 A1 | 8/2007 | Branch |
| 2007/0225806 A1 | 9/2007 | Squires et al. |
| 2007/0225812 A1 | 9/2007 | Gill |
| 2007/0233253 A1 | 10/2007 | Bray et al. |
| 2007/0250167 A1 | 10/2007 | Bray et al. |
| 2007/0255415 A1 | 11/2007 | Edie et al. |
| 2007/0270961 A1 | 11/2007 | Ferguson |
| 2007/0270963 A1 | 11/2007 | Melkent et al. |
| 2007/0270968 A1* | 11/2007 | Baynham .............. A61F 2/447 623/17.11 |
| 2008/0021559 A1 | 1/2008 | Thramann |
| 2008/0051890 A1 | 2/2008 | Waugh et al. |
| 2008/0051907 A1 | 2/2008 | Marik |
| 2008/0065222 A1 | 3/2008 | Hamada |
| 2008/0133013 A1 | 6/2008 | Duggal et al. |
| 2008/0140207 A1 | 6/2008 | Olmos et al. |
| 2008/0167657 A1 | 7/2008 | Greenhalgh |
| 2008/0183204 A1 | 7/2008 | Greenhalgh et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0076608 A1 | 3/2009 | Gordon et al. |
| 2009/0125062 A1 | 5/2009 | Arnin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0210062 A1 | 8/2009 | Thalgott et al. |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0179657 A1 | 7/2010 | Greenhalgh et al. |
| 2011/0035011 A1 | 2/2011 | Cain |
| 2011/0172774 A1 | 7/2011 | Varela |
| 2012/0059473 A1 | 3/2012 | Weiman |
| 2012/0158147 A1 | 6/2012 | Glerum et al. |
| 2012/0271422 A1 | 10/2012 | Miller et al. |
| 2013/0023994 A1 | 1/2013 | Glerum |
| 2013/0041471 A1 | 2/2013 | Siegal et al. |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 1382315 A1 | 1/2004 |
| FR | 2727003 A1 | 5/1996 |
| JP | 2006509560 A | 3/2006 |
| JP | 2007504843 A | 3/2007 |
| JP | 07213533 A | 8/2007 |
| JP | 2013508031 A | 3/2013 |
| JP | 2015533337 A | 11/2015 |
| SU | 1424826 A | 9/1988 |
| WO | 9201428 A1 | 2/1992 |
| WO | 9525485 A1 | 9/1995 |
| WO | 1997023175 A1 | 7/1997 |
| WO | 1999063914 A1 | 12/1999 |
| WO | 2005027040 A1 | 1/2005 |
| WO | 2007098288 A2 | 8/2007 |
| WO | 2008014258 A2 | 1/2008 |

OTHER PUBLICATIONS

U.S. Appl. No. 60/777,732, filed Feb. 27, 2006, Messerli et al.
U.S. Appl. No. 60/838,229, filed Aug. 16, 2006, Hunziker et al.
Guidance Document: Intervertebral Body Fusion Device, U.S. Dept. of Health and Human Services, Food and Drug Administration (Jun. 12, 2007).
M. Spruit et al.,The in vitro stabilizing effect of polyetheretherketone cages versus a titanium cage of similar design for anterior lumbar interbody fusion, 14(8) Eur. Spine J. 752, 752-758 (2005).
P. Schleicher et al., Biomechanical comparison of two different concepts for stand alone anterior lumbar interbody fusion, 17(12) Eur. Spine J. 1757, 1757-1765 (2008).
P.W. Pavlov et al., Anterior lumbar interbody fusion with threaded fusion cages and autologous bone grafts, 9 Eur. Spine J. 224, 224-229 (2000).
Synthes' SynFix Technique Guide device ("SynFix Technique Guide").

* cited by examiner

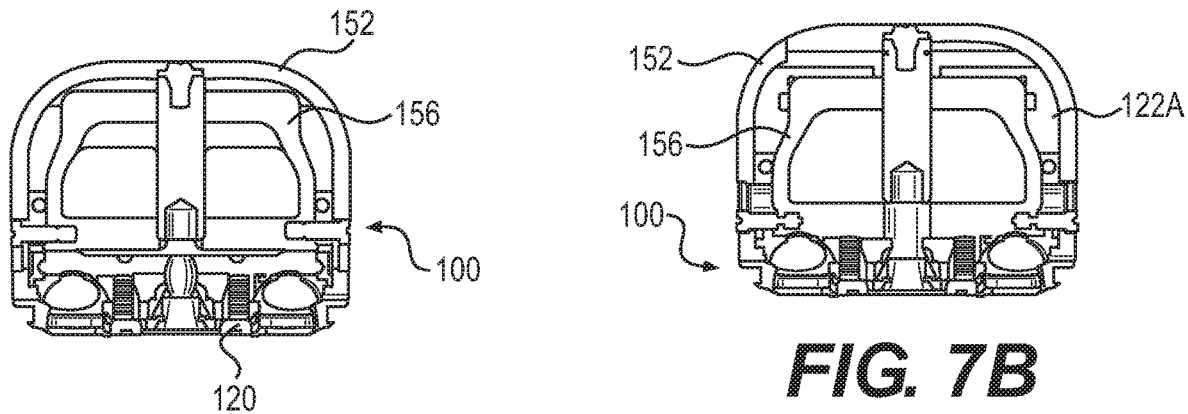
FIG. 7A
FIG. 7B
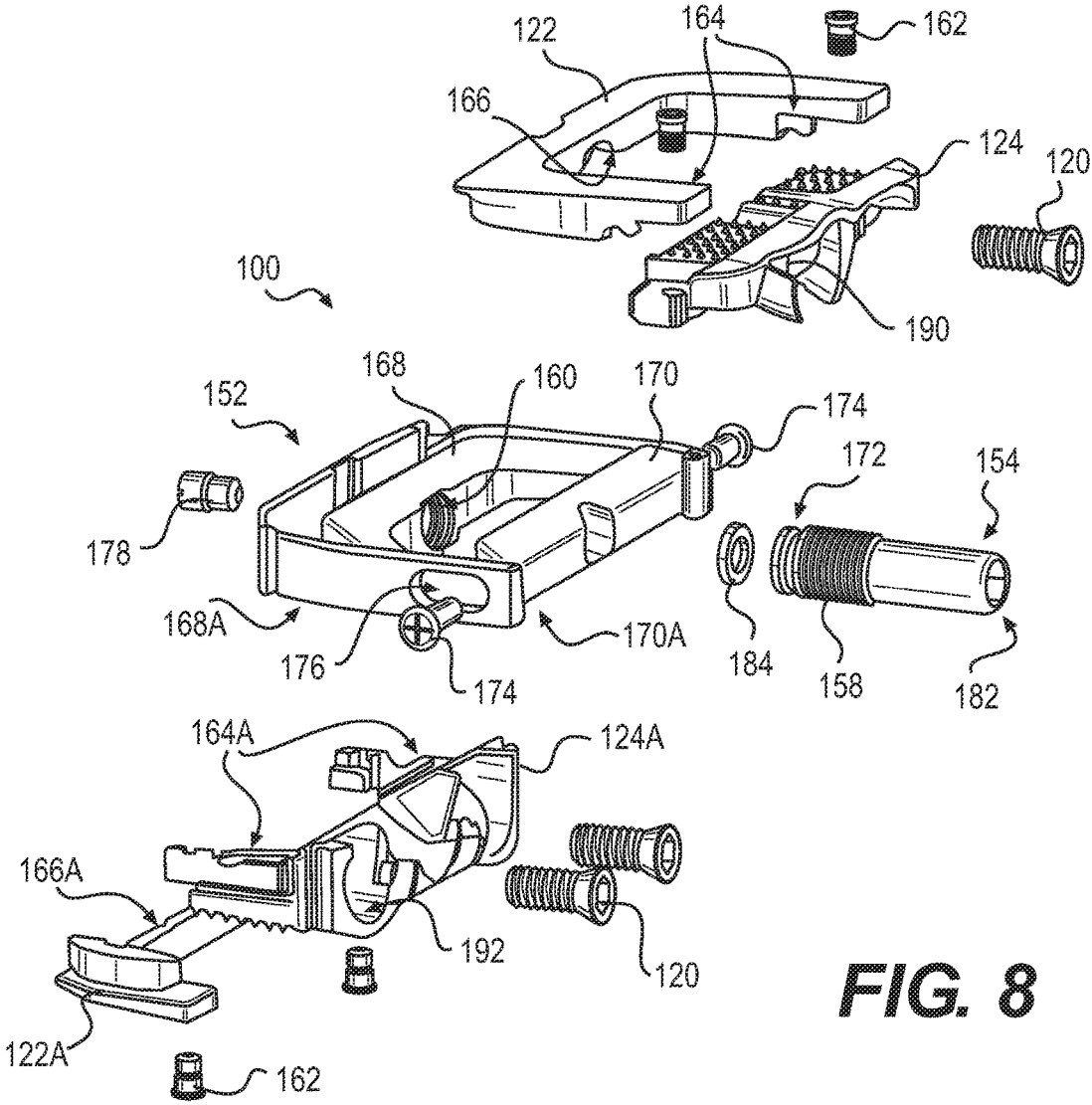
FIG. 8

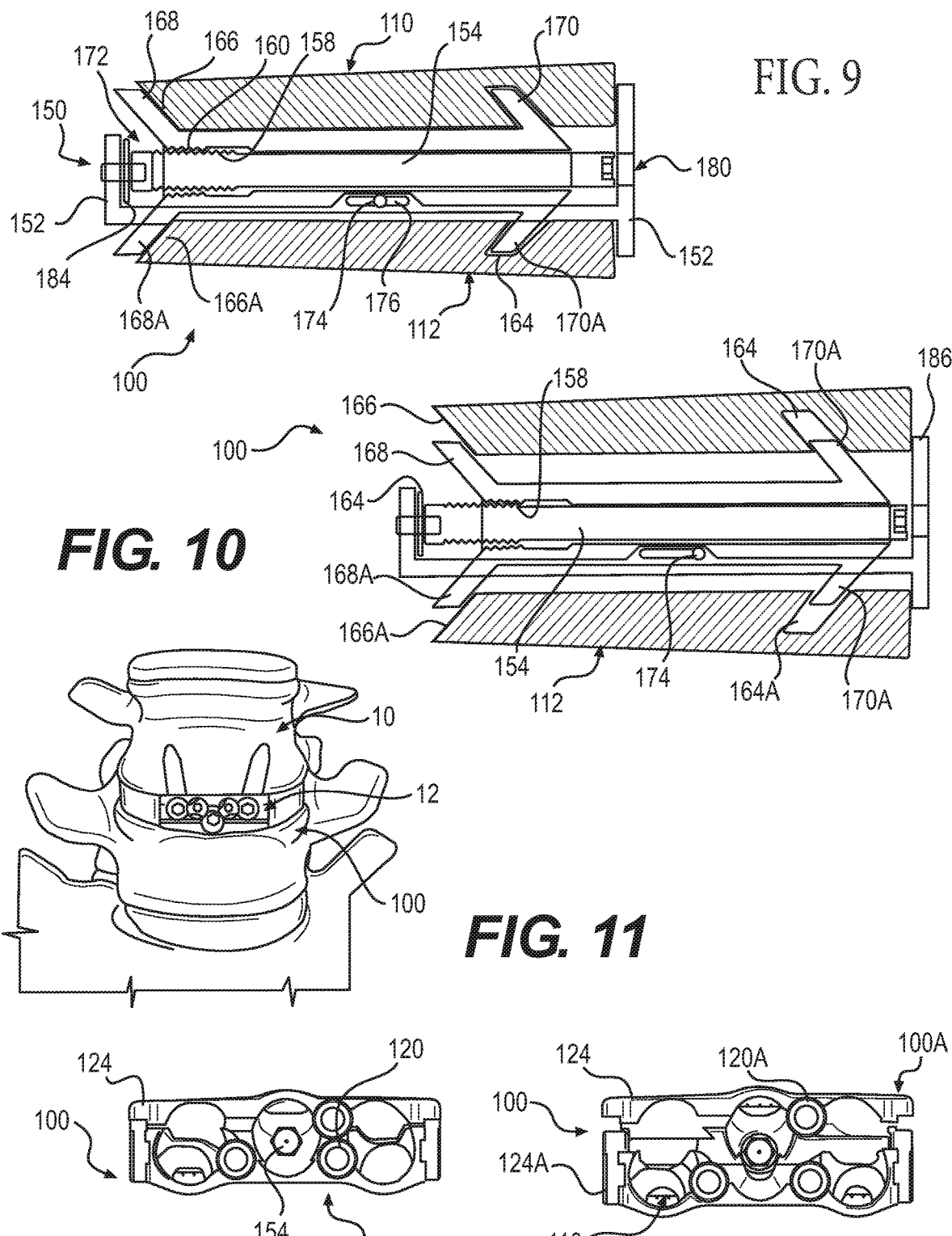

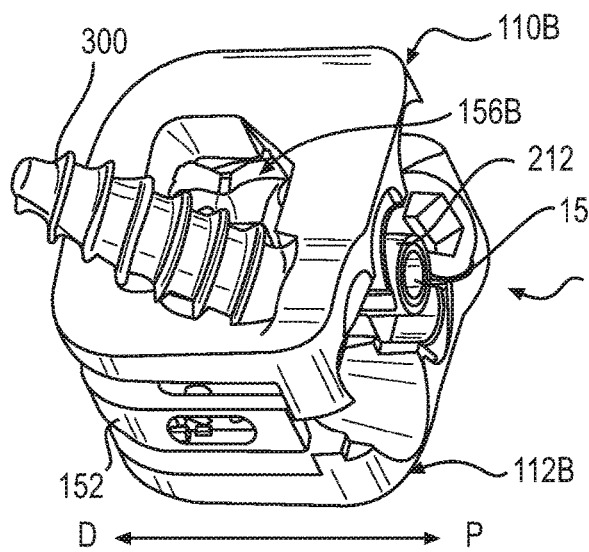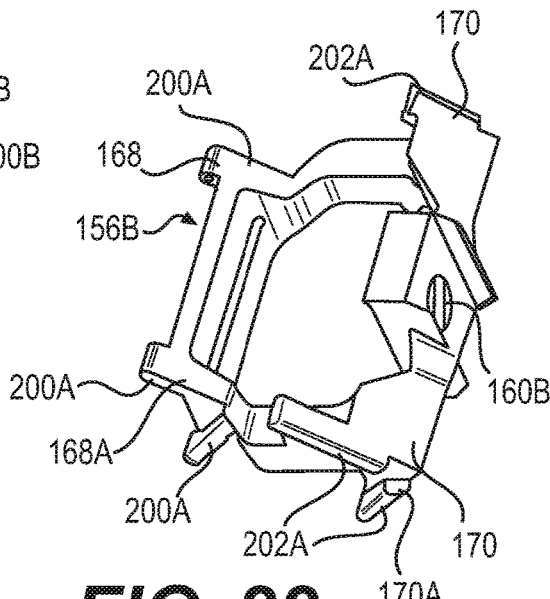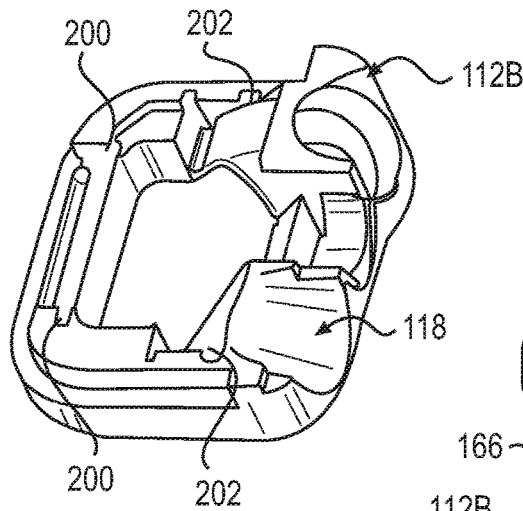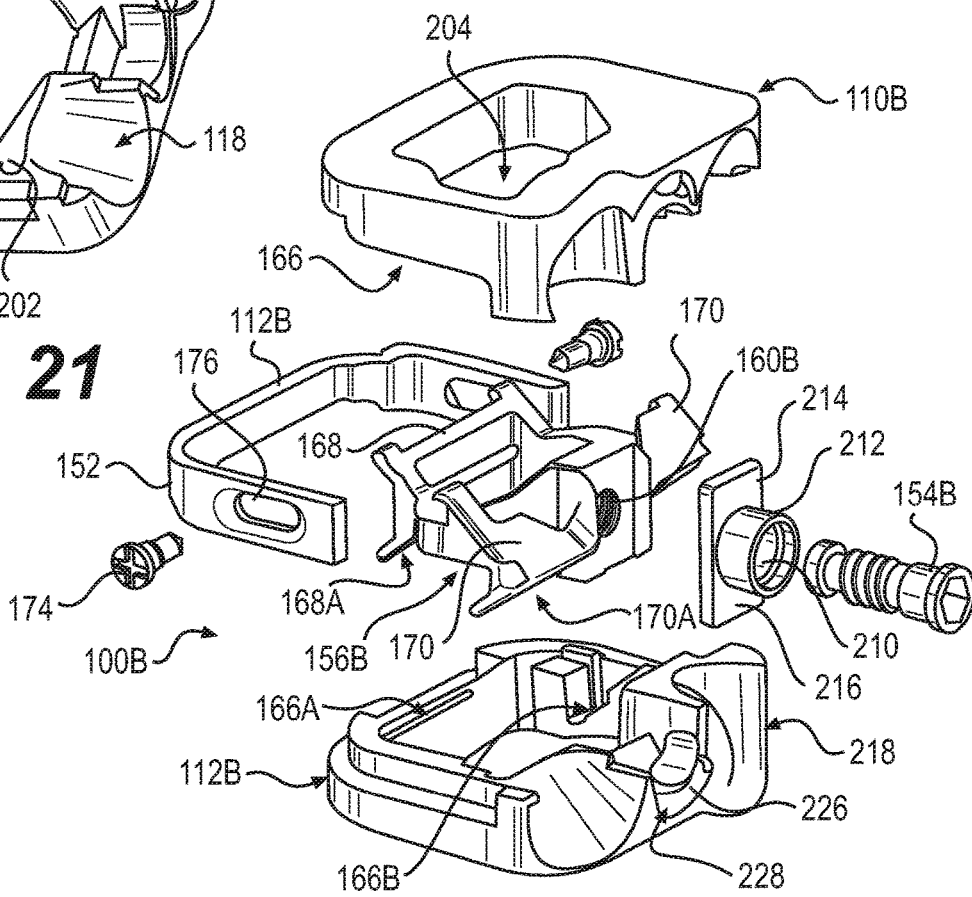

EXPANDABLE INTERVERTEBRAL IMPLANT

REFERENCE TO RELATED APPLICATIONS

The present application is a continuation of U.S. patent application Ser. No. 15/291,108 filed on Oct. 12, 2016, which is a continuation of U.S. patent application Ser. No. 14/676,323, filed Apr. 1, 2015, which is a continuation of U.S. patent application Ser. No. 13/836,005, filed Mar. 15, 2013, now U.S. Pat. No. 9,149,367. The references are incorporated by reference herein in their entirety.

FIELD OF THE INVENTION

This invention relates to stabilizing adjacent vertebrae of the spine by inserting an intervertebral implant, and more particularly an intervertebral implant that is adjustable in height.

BACKGROUND OF THE INVENTION

Bones and bony structures are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column requires additional support in order to address such weaknesses. One technique for providing support is to insert a spacer between adjacent vertebrae.

SUMMARY OF THE INVENTION

In accordance with the disclosure, an implant for therapeutically separating bones of a joint, the implant defining a longitudinal axis extending between distal and proximal ends, the implant comprises a first endplate configured to engage a first bone of the joint, and having an opening through the endplate, and at least one ramped surface on a side opposite a bone engaging side; a second endplate configured to engage a second bone of the joint, and having an opening through the endplate, and at least one ramped surface on a side opposite a bone engaging side; a frame slideably connected to the first and second endplates to enable the first and second endplates to move relative to each other at an angle with respect to the longitudinal axis, in sliding connection with the frame; an actuator screw rotatably connected to the frame; and a carriage (a) forming an open area aligned with the openings in the first and second endplates and defining thereby a proximal carriage side and a distal carriage side with respect to the longitudinal axis, (b) threadably connected to the actuator screw, whereby rotation of the actuator screw moves the carriage with respect to the frame and the first and second endplates, the actuator screw not crossing between the proximal carriage side and the distal carriage side; and (c) including a plurality of ramps each mateable with at least one of the at least one ramped surfaces of the first and second endplates, wherein when the carriage is moved by rotation of the actuator screw, at least one of the at least one ramped surface of the first endplate and at least one of the at least one ramped surface of the second endplate each slide along at least one of the plurality of ramps of the carriage to cause the endplates to move relative to each other in sliding connection with the frame.

In various embodiments thereof, the first and second endplates are confined by the frame to move relative to each other only along an axis substantially transverse to the longitudinal axis; at least one of the first and second endplates includes at least one aperture through which a fastener may pass to secure the implant to bone of the joint; the implant further includes a blocking mechanism configured to prevent backing out of a fastener passed through at least one of the first and second endplates and into body tissue; the blocking mechanism includes a blocking member slideably retained within a channel between an unblocking position and a blocking position in which a portion of the blocking member overlaps a portion of the faster; at least one of the first and second endplates includes one or more projections configured to engage bone of the joint when the implant is positioned between bones of the joint; at least one of the first and second endplates is composed of two interconnected portions of dissimilar materials; one of the dissimilar materials is metallic and includes at least one aperture through which a fastener may be passed to attach the implant to a bone of the joint; one dissimilar material is polymeric, and another dissimilar material is metallic; and, the implant further includes a polymeric material configured to press against the actuator screw to reduce a potential for unintended rotation of the actuator screw.

In further embodiments thereof, when the actuator screw is rotated in a first direction, a height of the implant transverse to the longitudinal axis is increased, and when the actuator screw is rotated in a second direction, a height of the implant transverse to the longitudinal axis is decreased; the actuator screw is threadably connected to the carriage along a proximal side of the carriage; the frame extends from the proximal end of the implant to the distal end of the implant, and the actuator screw is connected to the frame and threadably connected to the carriage along a distal side of the carriage; the frame is disposed within the proximal end of the implant; the frame extends from the proximal end of the implant towards the distal end of the implant; and, the implant further includes at least one post extending through the frame and into the carriage, slideably received in one of the frame or the carriage, thereby configured to maintain an alignment of the carriage along the longitudinal axis.

In yet further embodiments thereof, the implant further includes a first passage formed in a proximal end of at least one of the first and second endplates, and a second passage formed in a proximal side of the carriage, the first and second passages aligned to admit introduction of a therapeutic matter into the open area of the carriage when the implant is implanted between bones of the joint; the frame connects to the first and second endplates with a dovetail connection; the implant further includes at least one radiopaque marker positioned in connection with at least one of the first and second endplates, whereby an extent of movement of the connected endplate can be determined using imaging by a relative alignment of the radiopaque marker and a radiopaque element of the implant which does not move together with the connected endplate; ends of the at least one of the plurality of ramps of the carriage slide within grooves in at least one of the first and second endplates.

In another embodiment thereof, the frame includes an actuator screw bearing, a first tab extending away from the bearing in a first direction, and a second tab extending away from the bearing in a direction opposite to the upper tab, the first and second tabs forming edges; and the first and second endplates including grooves sized and dimensioned to slidingly receive the edges of the first and second tabs, respectively.

In accordance with another embodiment of the disclosure, an implant for therapeutically separating bones of a joint, the implant defining a longitudinal axis extending between distal and proximal ends, the implant comprises a first endplate configured to engage a first bone of the joint, and having an opening through the endplate transverse to the longitudinal axis, and at least one ramped surface on a side opposite a bone engaging side; a second endplate configured to engage a second bone of the joint, and having an opening through the endplate transverse to the longitudinal axis, and at least one ramped surface on a side opposite a bone engaging side;

a frame slideably connected to the first and second endplates to enable the first and second endplates to move relative to each other at an angle substantially transverse to the longitudinal axis, in sliding connection with the frame; an actuator screw rotatably connected to the frame; and a carriage (a) forming an open area aligned with the openings in the first and second endplates and defining thereby a proximal carriage side and a distal carriage side with respect to the longitudinal axis, (b) threadably connected to the actuator screw, whereby rotation of the actuator screw moves the carriage with respect to the frame and the first and second endplates, the actuator screw not crossing between the proximal carriage side and the distal carriage side; (c) including a plurality of ramps each mateable with at least one of the at least one ramped surfaces of the first and second endplates, wherein when the carriage is moved by rotation of the actuator screw, at least one of the at least one ramped surface of the first endplate and at least one of the at least one ramped surface of the second endplate each slide along at least one of the plurality of ramps of the carriage to cause the endplates to move relative to each other in sliding connection with the frame; and (d) at least one passage formed in a proximal side of the carriage in communication with at least one proximal passage in at least one of the first or second endplates, the communicating passages configured to admit introduction of a therapeutic matter into the open area of the carriage when the implant is implanted between bones of the joint.

In accordance with the disclosure, a method of therapeutically separating bones of a joint, comprises inserting an implant defining a longitudinal axis extending between distal and proximal ends between bones of the joint, the implant including—a first endplate configured to engage a first bone of the joint, and having an opening through the endplate, and at least one ramped surface on a side opposite a bone engaging side; a second endplate configured to engage a second bone of the joint, and having an opening through the endplate, and at least one ramped surface on a side opposite a bone engaging side; a frame slideably connected to the first and second endplates to enable the first and second endplates to move relative to each other at an angle with respect to the longitudinal axis, in sliding connection with the frame; an actuator screw rotatably connected to the frame; and a carriage (a) forming an open area aligned with the openings in the first and second endplates and defining thereby a proximal carriage side and a distal carriage side with respect to the longitudinal axis, (b) threadably connected to the actuator screw, whereby rotation of the actuator screw moves the carriage with respect to the frame and the first and second endplates, the actuator screw not crossing between the proximal carriage side and the distal carriage side; and (c) including a plurality of ramps each mateable with at least one of the at least one ramped surfaces of the first and second endplates, wherein when the carriage is moved by rotation of the actuator screw, at least one of the at least one ramped surface of the first endplate and at least one of the at least one ramped surface of the second endplate each slide along at least one of the plurality of ramps of the carriage to cause the endplates to move relative to each other in sliding connection with the frame; and rotating the actuator screw after the implant is inserted to move the first and second endplates relatively farther apart to separate bones of the joint.

BRIEF DESCRIPTION OF THE DRAWINGS

A more complete understanding of the present invention, and the attendant advantages and features thereof, will be more readily understood by reference to the following detailed description when considered in conjunction with the accompanying drawings, in which:

FIG. 7A depicts an transverse cross-section of the implant of FIG. 2;

FIG. 7B depicts an transverse cross-section of the implant of FIG. 3;

FIG. 8 depicts an exploded view of the implant of FIG. 1;

FIG. 9 depicts a diagrammatic view of aspects of an implant in accordance with the disclosure, in a reduced height configuration;

FIG. 10 depicts a the implant of FIG. 9, in an expanded height configuration;

FIG. 11 depicts the implant of FIG. 1, implanted between adjacent vertebrae;

FIG. 12A depicts a front view of the implant of FIG. 1 having an alternative blocking configuration, in a reduced height configuration;

FIG. 12B depicts the implant of FIG. 12A in an expanded height configuration;

FIG. 19 depicts an implant of the disclosure including a proximally driven carriage;

FIG. 20 depicts the carriage of the implant of FIG. 19;

FIG. 21 depicts a lower endplate of the implant of FIG. 19;

FIG. 22 depicts an exploded view of the implant of FIG. 19;

DETAILED DESCRIPTION OF THE INVENTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

Implants of the disclosure allow continuous expansion and retraction within a range of expansion. Lordosis of certain embodiments of implants herein can be custom tailored to fit the anatomy of a specific patient. Additionally, implants of the disclosure enable distraction of vertebral bodies to a desired height, but can also be collapsed and repositioned, as therapeutically indicated for the patient.

Figure 1:
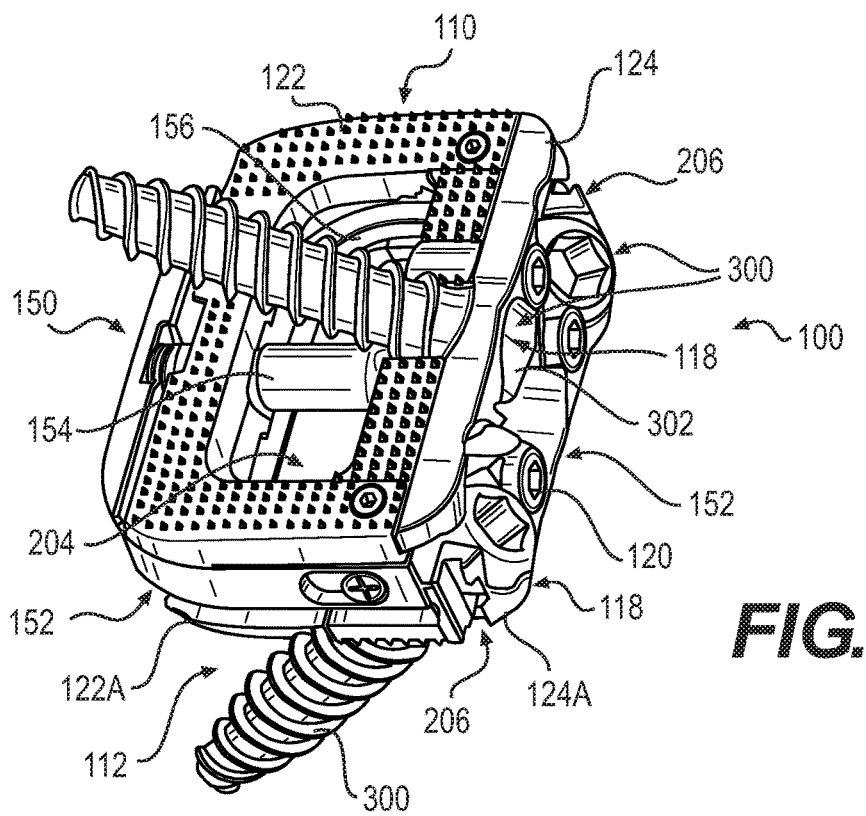
FIG. 1 depicts an implant of the disclosure, together with three mounted bone screws.
Figure 2:
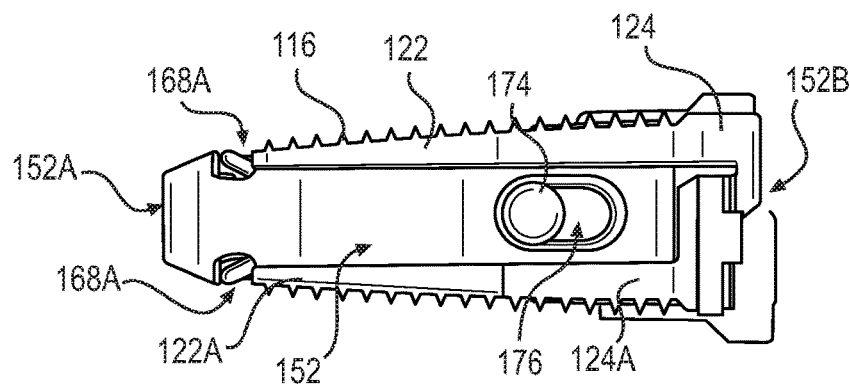
FIG. 2 depicts the implant of FIG. 1, in a compressed or reduced height configuration.
Figure 3:
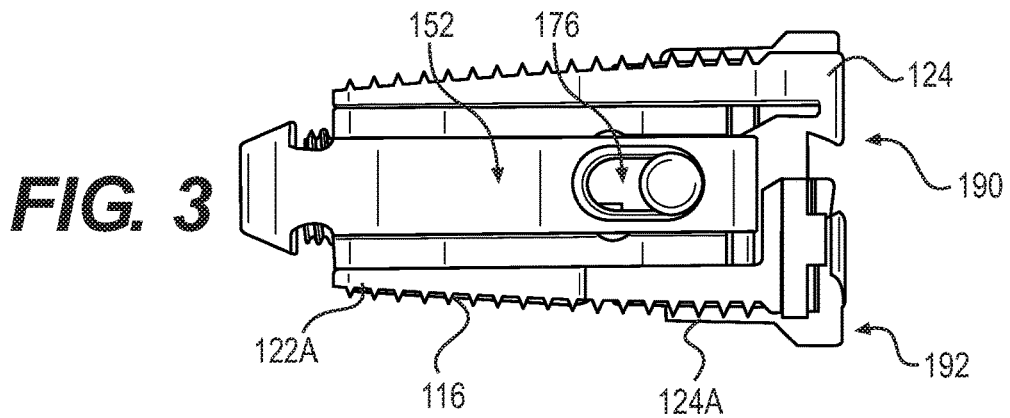
FIG. 3 depicts the implant of FIG. 1, in an expanded or increased height configuration.
Figure 4:
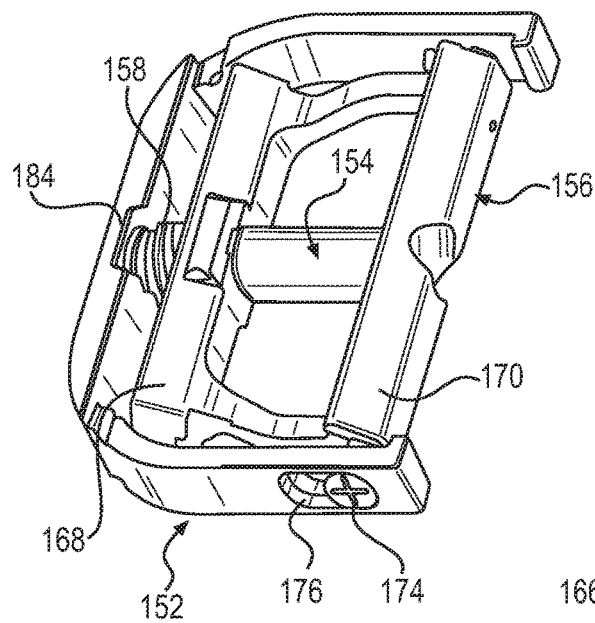
FIG. 4 depicts a carriage and frame of the implant of FIG. 1.
Figure 5:
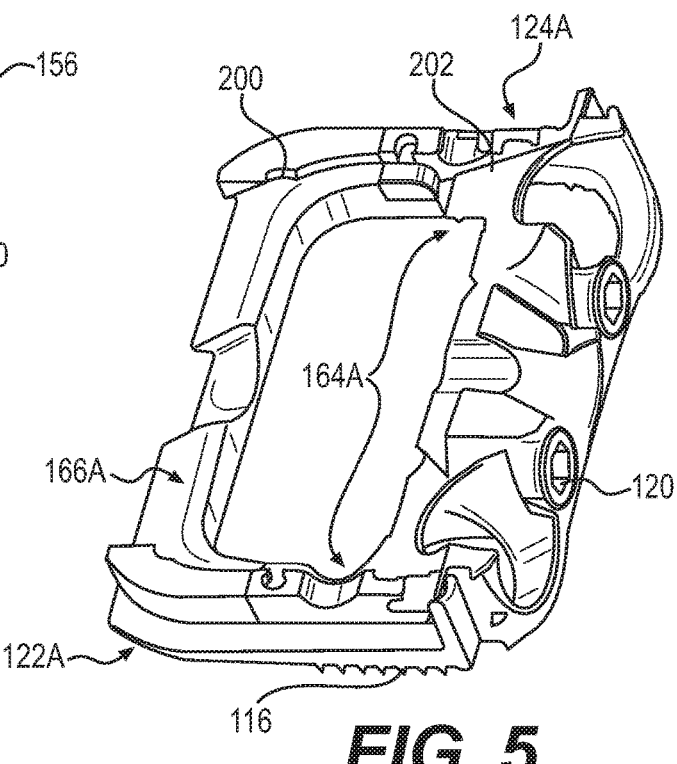
FIG. 5 depicts an endplate of the implant of FIG. 1.
Figure 6A:
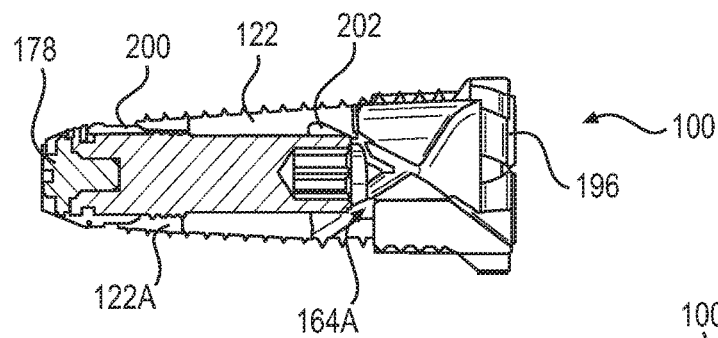
FIG. 6A depicts a sagittal cross-section of the implant of FIG. 2.
Figure 6B:
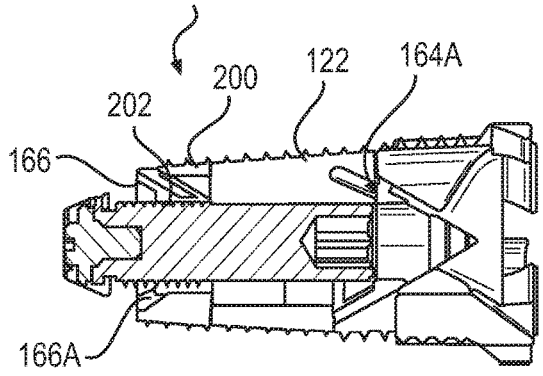
FIG. 6B depicts a sagittal cross-section of the implant of FIG. 3.
Figure 13:
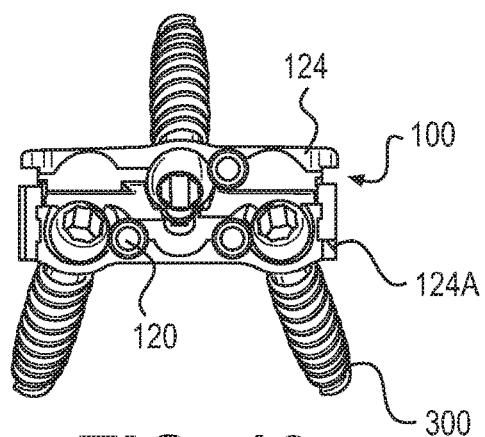
FIG. 13 depicts the implant of FIG. 12B, with bones screws inserted into the implant.

With reference to FIGS. 1-3, implant or implant 100 is operative, when positioned between adjacent bones of a joint, such as for example vertebrae 10, 12 (shown in FIG. 11), to stabilize a joint formed by adjacent vertebrae. Implant 100 has a collapsed state or height, illustrated in FIG. 2, and an expanded state or height, illustrated in FIG. 3. Implants 100 of the disclosure may be inset into the intervertebral disc space at a collapsed height, and then expand axially (superior/inferior) to restore height loss in the disc space. The implant provides distraction as well as achieves optimal height restoration. When inserted in a collapsed state, implants 100 reduce impaction to tissue in the joint space during insertion, and form the least visually blocking or obstructing profile.

Implant 100 includes two separable endplates 110, 112. A surface 114 of an endplate 110, 112 can be provided with teeth or other projections 116 which can penetrate body tissue to reduce a likelihood of migration of implant 100 after implantation. Implant 100 is further secured with one or more bone screws 300, which pass through bone screw socket 118 within implant 100, and into body tissue of the patient. In the embodiment illustrated in FIGS. 1-3, three sockets 118 for three bone screws are provided, the bone screws 300 further retained in connection with implant 100 by blocking fasteners 120. Bone screw 300 can be a polyaxial screw, and sockets 118 correspondingly shaped, whereby bone screw 300 may be inserted into body tissue at an optimal angle with respect to implant 100, whereby optimal purchase may be obtained, or certain body tissue may be avoided.

Endplates 110, 112 are moveably connectable to an actuator 150 operable to change a relative relationship of endplates 110 and 112. Actuator 150 includes a frame 152 rotatably supporting an actuator screw 154, and a moveable carriage 156. As actuator screw 154 rotates within frame 152, carriage 156 slides within frame 152, driven by cooperation between threads 158 (FIG. 8) upon actuator screw 154, and mating threads 160 within carriage 156. In the embodiment of FIGS. 1-3, endplates 110 and 112 are formed in two connected portions, including a portion 122, 122A which can be polymeric, and a portion 124, 124A, which can be metallic. The portions are joined in the embodiment shown by screws 162, although other methods of combining the two connected portions 122, 124 or 122A and 124A may be used, including a dovetail connection, or adhesive, possibly in combination with each other, or with endplate connector screws 162. Metallic portions 124, 124A can provide greater strength for portions of implant 100 which are under relatively greater stress, for example portions through which a fastener may pass to anchor implant 100 within the body. While portions 122, 122A, 124, 124A are described as polymeric or metallic, it should be understood that other materials may be used, and that the portions can be of dissimilar materials.

With reference to FIG. 2, it may be seen that implant 100 is in a compressed state, having a lower height relative to an expanded state, as shown in FIG. 3. A functioning of device 100 may be best understood with reference to FIGS. 9-10, which correlate with FIGS. 2-3, respectively, but which present a simplified view having certain elements eliminated or exaggerated, to ease understanding. Endplates 110 and 112 are provided with ramped channels 164, 164A, and an open ramp 166, 166A, sized to slidingly receive ramps 168, 168A and 170, 170A disposed upon carriage 156. While two mating channels and ramps are illustrated for each endplate 110, 112, it should be understood that one, or more than two, sets of channels and or ramps may be provided. Further, channels 164, 164A may alternatively be formed as ramps. However, a channel can operate to enable a reduction of height, having an opposing ramp face, whereby rotation of actuator screw 154 in an opposite direction to expansion can drive endplates 110, 112 together, for example when pressure from body tissue is insufficient to collapse endplates 110, 112. Additionally, at least one channel can operate to foster the maintenance of a connection between carriage 156 and an endplate 110, 112.

Carriage 156 is supported by frame 152 by lateral engagement means, in this embodiment two support screws 174 engaged with carriage 156, and passable through respective channels 176 formed in frame 152. Distal end 172 of actuator screw 154 provides additional support for carriage 156. Actuator screw 154 is supported by a set screw 178, which passes through and is rotatably supported within frame 152.

An actuator access port 180 permits passage of a tool, for example a hex driver (not shown), into engagement with a proximal end 182 of actuator screw 154. As actuator screw 154 is turned, distal end 172 bears against a thrust washer 184, and an end portion of frame 152. As actuator screw 154, carriage 156 is driven along actuator screw by interaction of threads 158 and 160. As carriage 156 moves, endplates 110, 112 are urged to move along ramps 168, 168A and 170, 170A, moving relatively apart, and increasing a height of implant 100. Endplates 110, 112 are prevented from moving together with carriage 156 by abutting against an end portion 186 of frame 152. In a given orientation, one of endplate 110 and 112 is an upper endplate with respect to an orientation in a standing patient. However, implant 100 may, in some embodiments, be implantable in either of opposite orientations, and therefore designations of upper and lower are provided for ease of understanding, only. It should be understood that only one of endplate 110, 112 may be moveable with respect to the other. For example, in one embodiment, ramps 168A, 170A may not be provided, and endplate 112 may be attached to frame 152.

FIG. 11 illustrates an implant 100 of the disclosure implanted between adjacent vertebrae 10, 12. Frame 152 defines a distal or leading end 152A which is inserted first into the body, and a proximal or trailing end 152B which passes last into the body, the distal and proximal ends defining a longitudinal axis extending therebetween. Implant 100 can be inserted into the body, and into a position between vertebrae, using minimally invasive methods, for example using a small incision, and implant 100 may be passed through a cannula or other structure which maintains a pathway through body tissue. Implant 100 may be inserted into the spinal column through any approach, including anterior, anterolateral, lateral, or posterolateral. A portion of the disc annulus, and nucleus pulposus may be removed in order to form a space into which implant 100 may be inserted. When implant 100 is in a compressed, or reduced height configuration, dovetail guides 200, 202 can be provided to foster maintenance of a relative orientation of upper and lower endplates during insertion or removal of device 100. Dovetail guides 200, 202 further stabilize endplates 110, 112 during expansion, and when implant 100 is expanded. Dovetail guides 200, 202, can have the form of a tongue and groove configuration, or other sliding mating configuration, with ends of ramps 168, 168A, for example.

Implant 100 can be inserted configured to have a lower height profile, as shown in FIG. 2, whereby an extent of distraction of body tissue may be reduced during insertion. Moreover, to the extent that implant 100 is used to open a pathway towards an implantation site, trauma to adjacent tissue is reduced relative to inserting an implant having a final height profile. Once implant 100 is positioned between adjacent vertebrae, actuator screw is rotated by a tool. The tool may be positioned entirely within the body, or can extend from in interior of the body to outside the body, for example having a driving tip at one end and having a handle at an opposite end, with a shaft extending into the body between each end.

Once actuator screw 154 has been rotated to separate endplates 110, 112 a desired amount, the tool is removed. At this point, actuator screw 154 may be secured in place, for example using a mechanical block, or an adhesive, to prevent unintended rotation of actuator screw 154. As carriage 156 is slideably moved by rotation of actuator screw 154, a ramp 166, 166A or a ramped surface of channel 164, 164A of at least one of endplate 110, 112 slides against at least one ramp 168, 168A, 170, or 170A of carriage 156, to cause the endplate to move along an axis transverse to the longitudinal axis of the frame, to increase a height of the implant. Rotation of actuator screw 154 in an opposite direction causes movement along an axis transverse to the longitudinal axis of the frame to decrease a height of the implant.

Polymeric insets, or a polymeric square nut, for example PEEK, can be provided, engageable with threads 158 or other portion of actuator screw 154, to provide additional friction to prevent height loss under load, particularly under cyclic loading. Similarly, once bone screws 300 have been inserted, blocking elements 120 may be rotated to extend over an end of bone screw head 302, preventing screw 300 from backing out. A similar mechanical block (not shown) may be provided for actuator screw 154.

With reference to FIGS. 1-3, 5-8, it may be seen that a socket 118 for a polyaxial screw head 302 can be formed entirely within one of upper or lower endplate 110, 112, or may be formed partially within each of endplate 110 and 112, whereby when implant 100 has been expanded to a final height, the proportions of an interior of socket 118 are correct or substantially correct for retaining screw head 302. For example, in FIG. 8, metallic portion 124 forms an upper portion 190 of socket 118, and mating metallic portion 124A forms a lower portion 192 of socket 118. In the embodiment illustrated in the figures, there are three sockets 118, and all are formed of upper and lower portions. However, there may be more or fewer sockets 118, and one or more sockets may be formed entirely in an upper or lower endplate.

In an embodiment, implant 100 of the disclosure provides an actuator that translates relative to the body by means of a threaded actuator screw 154. Ramps 168, 168A and 170, 170A on a carrier 152 mate with channels 164, 164A, and or ramps 166, on endplates 110, 112. Linear translation of carriage 156 causes endplates 110, 112 to expand implant 100 along an S/I axis with respect to the body. There can be dovetail guides that capture endplates 110, 112 when collapsing the implant.

Assembly screws 162 fasten endplates made of dissimilar materials, for example PEEK polymeric portions 122, 122A to Titanium metallic portions 124, 124A. A dovetail and press fit design can be used to connect the dissimilar endplate portions. A PEEK bushing or washer 184 is used between the threaded actuator screw 154 and frame 152 to minimize friction during expansion of implant 100. Support screws 174 and channels 176 cooperate to form side or lateral stabilizers, and set screw 178 supports a nose or leading end of carriage 156. Additionally, cooperating slots and projections (not shown) in carriage 156 and frame 152 can be provided for further relative guidance and stability.

In one embodiment, three bone screws 300 are used to provide fixation into adjacent vertebral bodies, two screws 300 passing through implant 100 and into one vertebra, and one screw 300 passing through implant 100 into another vertebra, although other combinations may be used. Bone screws 300 can have spherical or otherwise curved heads, facilitating insertion at a desired angle, or may be provided to mate with socket 118 in a fixed orientation, particularly depending on a diameter of a neck portion of screw 300. Cam style blocking fasteners 120 can be used to block bone screws 300 from backing out after being inserted.

Implants of the disclosure enable a continuous expansion and retraction over a range of displacements according to predetermined dimensions of a specific implant 100 design. This provides the ability to distract vertebral bodies to a desired height, but also to collapse the implant 100 for repositioning, if therapeutically advantageous for the patient. Endplates 110, 112 may be shaped to form planes or surfaces which converge relative to each, to provide for lordosis, and can be provided with openings, forming a graft chamber 204 through the openings and between the respective openings through which bone may grow, and into which bone graft material may be placed. Implant 100 may be used to distract, or force bones of a joint apart, or may be used to maintain a separation of bones created by other means, for example a retractor.

Implant 100 may be fabricated using any biocompatible materials known to one skilled in the art, having sufficient strength, flexibility, resiliency, and durability for the patient, and for the term during which the device is to be implanted. Examples include but are not limited to metal, such as, for example titanium and chromium alloys; polymers, including for example, PEEK or high molecular weight polyethylene (HMWPE); and ceramics. There are many other biocompatible materials which may be used, including other plastics and metals, as well as fabrication using living or preserved tissue, including autograft, allograft, and xenograft material.

Portions or all of the implant may be radiopaque or radiolucent, or materials having such properties may be added or incorporated into the implant to improve imaging of the device during and after implantation.

For example, metallic portions 124, 124A of endplates 110, 112 may be manufactured from Titanium, or a cobalt-chrome-molybdenum alloy, Co—Cr—Mo, for example as specified in ASTM F1537 (and ISO 5832-12). The smooth surfaces may be plasma sprayed with commercially pure titanium, as specified in ASTM F1580, F1978, F1147 and C-633 (and ISO 5832-2). Polymeric portions 122, 122A may be manufactured from ultra-high molecular weight polyethylene, UHMWPE, for example as specified in ASTM F648 (and ISO 5834-2). In one embodiment, PEEK-OPTIMA (a trademark of Invibio Ltd Corp, United Kingdom) may be used for one or more components of implant 100. For example, polymeric portions 122, 122A can be formed with PEEK-OPTIMA, which is radiolucent, whereby bony ingrowth may be observed. Other polymeric materials with suitable flexibility, durability, and biocompatibility may also be used.

In accordance with the invention, implants of various sizes may be provided to best fit the anatomy of the patient. Components of matching or divergent sizes may be assembled during the implantation procedure by a medical practitioner as best meets the therapeutic needs of the patient, the assembly inserted within the body using an insertion tool. Implants of the invention may also be provided with an overall angular geometry, for example an angular mating disposition of endplates 110, 112, to provide for a natural lordosis, or a corrective lordosis, for example of from 0° to 6° for a cervical application, although much different values may be advantageous for other joints. Lordotic angles may also be formed by shaping one or both of plates 110, 112 to have relatively non-coplanar surfaces. Expanded implant heights, for use in the cervical vertebrae for example, may typically range from 7 mm to 12 mm, but may be larger or smaller, including as small as 5 mm, and as large as 16 mm, although the size is dependent on the patient, and the joint into which an implant of the invention is to be implanted. Implants 100 may be implanted within any level of the spine, and may also be implanted in other joints of the body, including joints of the hand, wrist, elbow, shoulder, hip, knee, ankle, or foot.

In accordance with the invention, a single implant 100 may be used, to provide stabilization for a weakened joint or joint portion. Alternatively, two, three, or more implants 100 may be used, at a single joint level, or in multiple joints. Moreover, implants 100 may be combined with other stabilizing means.

Additionally, implant 100 may be fabricated using material that biodegrades in the body during a therapeutically advantageous time interval, for example after sufficient bone ingrowth has taken place. Further, implant 100 is advantageously provided with smooth and or rounded exterior surfaces, which reduce a potential for deleterious mechanical effects on neighboring tissues.

Any surface or component of the invention may be coated with or impregnated with therapeutic agents, including bone growth, healing, antimicrobial, or drug materials, which may be released at a therapeutic rate, using methods known to those skilled in the art.

Devices of the disclosure provide for adjacent vertebrae to be supported during flexion/extension, lateral bending, and axial rotation. In one embodiment, implant 100 is indicated for spinal arthroplasty in treating skeletally mature patients with degenerative disc disease, primary or recurrent disc herniation, spinal stenosis, or spondylosis in the lumbosacral spine (LI-SI). Degenerative disc disease is advantageously defined as discogenic back pain with degeneration of the disc confirmed by patient history and radiographic studies, with or without leg (radicular) pain. Patients are advantageously treated, for example, who may have spondylolisthesis up to Grade 1 at the involved level. The surgery position implant 100 may be performed through an Anterior, Anterolateral, Posterolateral, and/or Lateral approach.

In a typical embodiment, implant 100 has a uncompressed height, before insertion, of 12 to 18 mm, and may advantageously be provided in cross-sections of 23×32 mm, 26×38 mm and 26×42 mm, with 4, 8, 12, or 16 degree lordotic angles, although these are only representative sizes, and substantially smaller or larger sizes can be therapeutically beneficial. In one embodiment an implant 100 in accordance with the instant disclosure is sized to be inserted using an MIS approach (a reduced incision size, with fewer and shorter cuts through body tissue).

Implant 100 may advantageously be used in combination with other known or hereinafter developed forms of stabilization or fixation, including for example rods and plates.

Referring now to FIGS. 13-18, implant 100 can be insert it into the intervertebral disc space at a collapsed height, and then expand it to restore the disc space height. Implant 100 provides distraction as well as achieves optimal sagittal balance. As discussed, there are multiple methods and approaches by which implant 100 can be inserted. FIGS. 14-18 illustrate one possible method and approach of the disclosure. While a series of numbered steps are described, it should be understood that there can be numerous other steps pertaining to the procedure, and that the steps described emphasize useful steps in the deployment of implant 100 of the disclosure.

Step 1: Approach—An approach to the desired section of the spine is performed using surgical instruments such as scalpels and retractors, for example using minimally invasive techniques.

Step 2: Preparation—Disc preparation instruments can be used to expose the disc and remove disc material, for example using rongeurs and other suitable instruments (not shown), to create a disc space 14.

Figure 14:
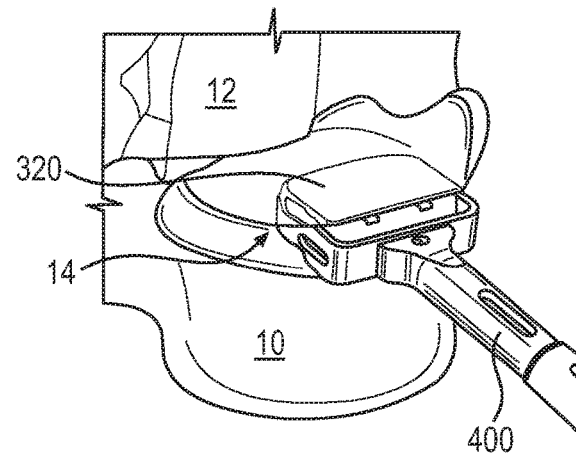
FIG. 14 depicts inserting a trial of the disclosure, the trial representing an implant of the disclosure, into the disc space, using a trialing tool of the disclosure.
Figure 15:
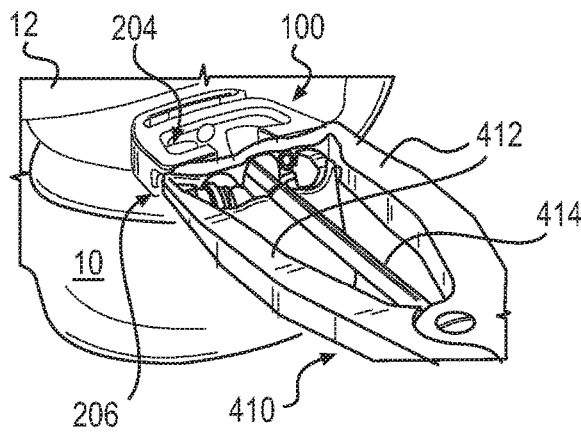
FIG. 15 depicts an implantation and actuating tool of the disclosure inserting an implant of the disclosure into the disc space.
Figure 16:
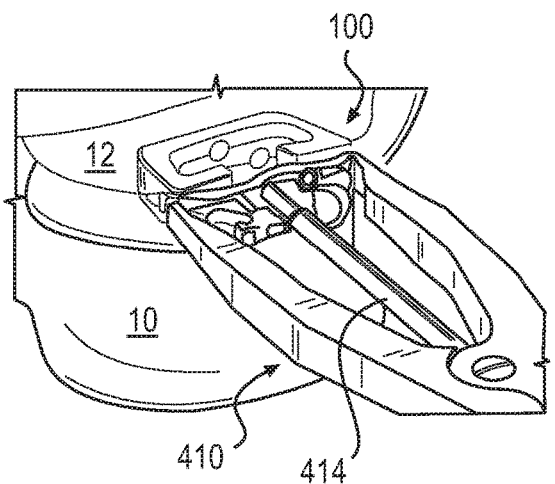
FIG. 16 depicts the implant and tool of FIG. 14, the tool having expanded the implant.
Figure 17:
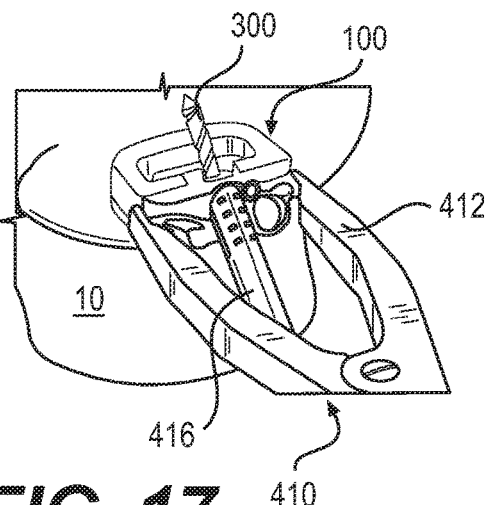
FIG. 17 depicts the implant and tool of FIG. 15, and a bone screw driver inserting a bone screw.

Step 3: Trialing—As may be seen in FIG. 14, trialing for implant footprint, height and wedge angle is performed to indicate which size or type of implant 100 is to be used. An expandable trial, static trials, or a combination of each may be used. In FIG. 14, trial implant 320 is trial fit using trial insertion tool 400.

Step 4: Insertion—Graft material or other therapeutically beneficial material is packed into graft chamber 204 of the selected implant 100 when it is collapsed or partially expanded. As may be seen in FIG. 15, implant 100 is inserted into disc space 14 using insertion tool 410. Tool engagement formations 206 are provided on opposite sides of frame 152 or one of endplate 124 or 124A, as can be seen in FIG. 1. Tool arms 412 securely and releasably engage tool engagement formations 206, and align an expansion driver 414 with actuator screw 154.

Figure 40:
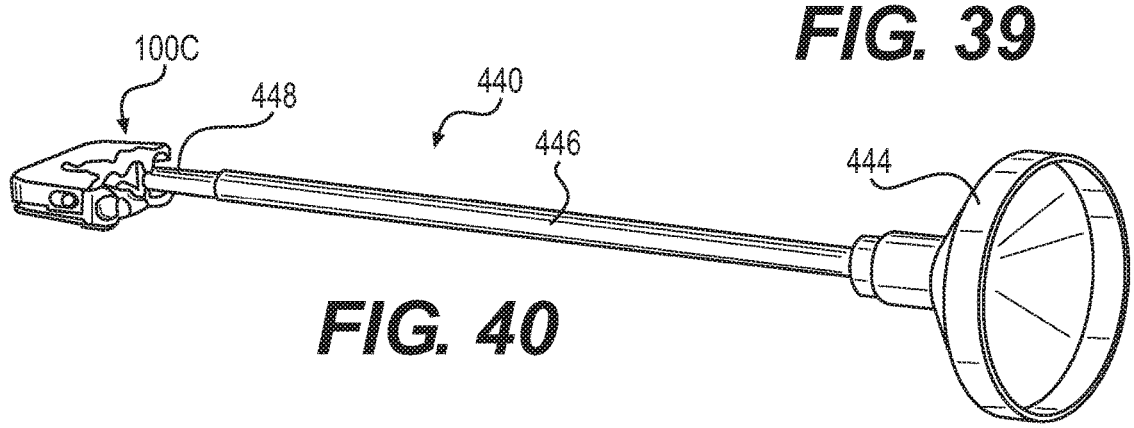
FIG. 40 depicts a bone funnel of the disclosure, used in connection with an implant of the disclosure.

Step 5: Expansion—In FIG. 16, implant 100 is expanded, as described herein, by turning actuator screw 154 using expansion driver 414. After expansion, additional bone graft material can be packed through graft portals 208 into the central graft chamber 204 using a bone funnel 440 (FIG. 40). A push rod (not shown) can be used for driving graft material through funnel 440.

Step 6: Hole Preparation—Bone screw pilot holes can be formed into one or more adjacent vertebrae, prepared using, for example, awls, drills and or taps. Multiple pilot holes can be prepared first, or pilot holes can be prepared one at a time, before the insertion of each screw 300. During any of the steps herein, imaging can be carried out to avoid damage to adjacent tissue.

Figure 18:
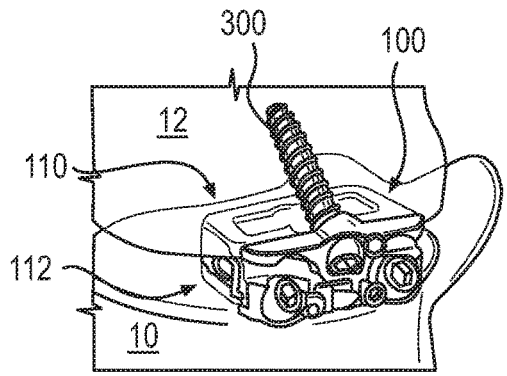
FIG. 18 depicts the implant of FIG. 13 secured between vertebrae.
Figure 23:
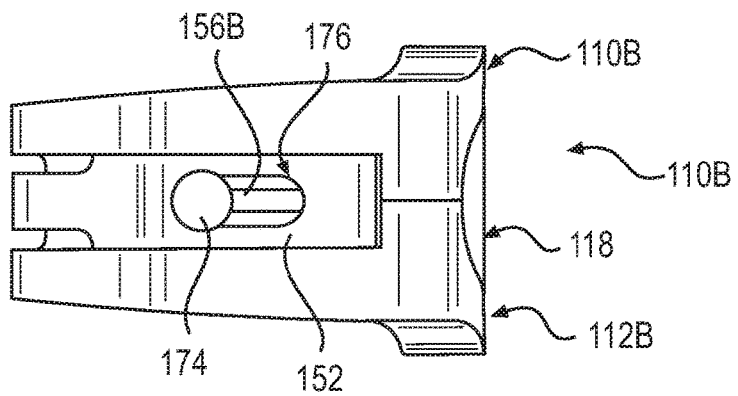
FIG. 23 depicts a reduced height configuration of the implant of FIG. 19.
Figure 24:
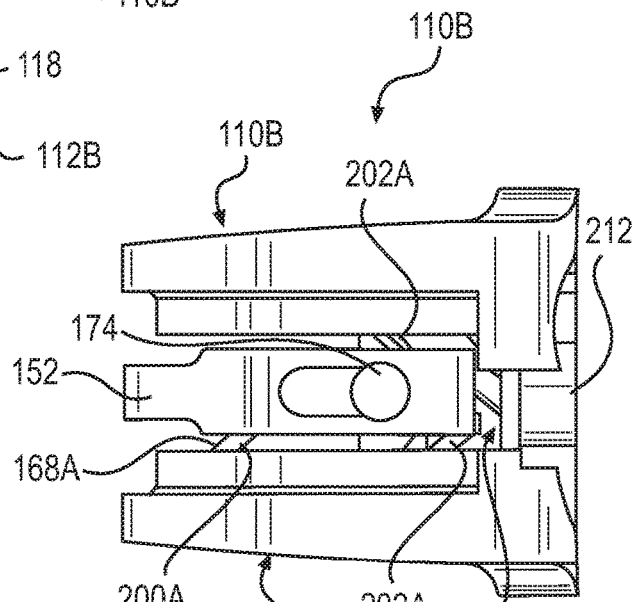
FIG. 24 depicts an expanded height configuration of the implant of FIG. 23.
Figure 25:
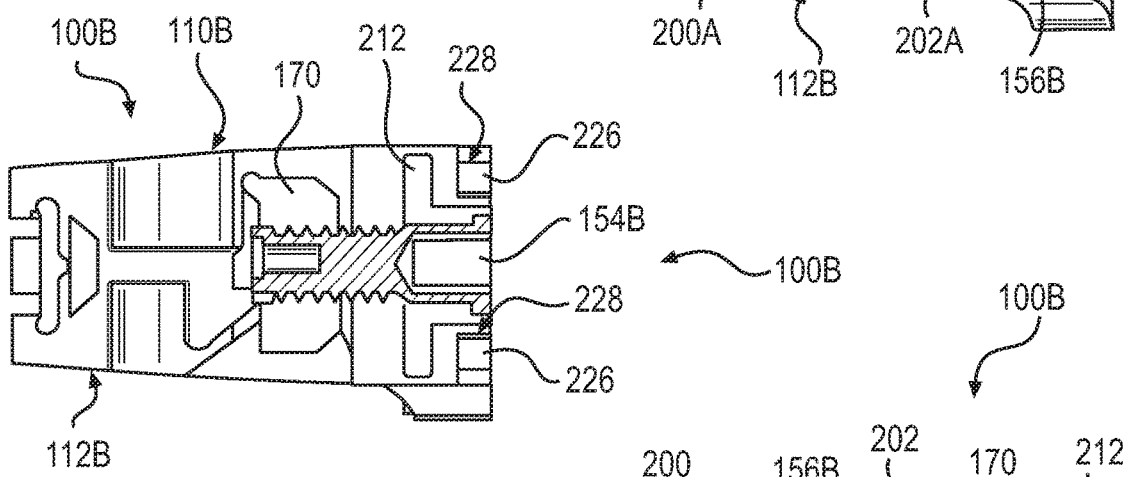
FIG. 25 depicts a cross section of the implant of FIG. 23.
Figure 26:
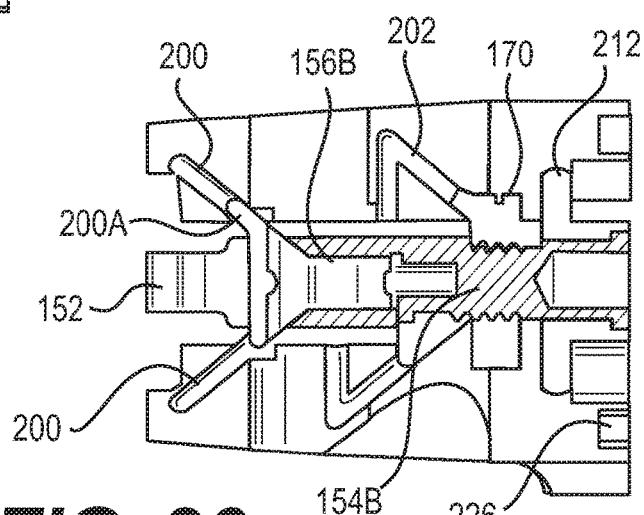
FIG. 26 depicts a cross section of the implant of FIG. 24.
Figure 27:
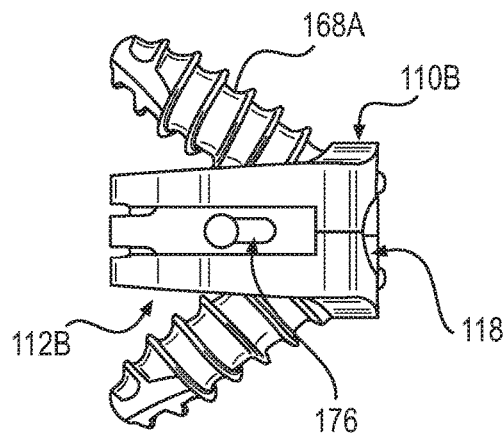
FIG. 27 depicts the implant of FIG. 23, with bone screws inserted into the implant.
Figure 28:
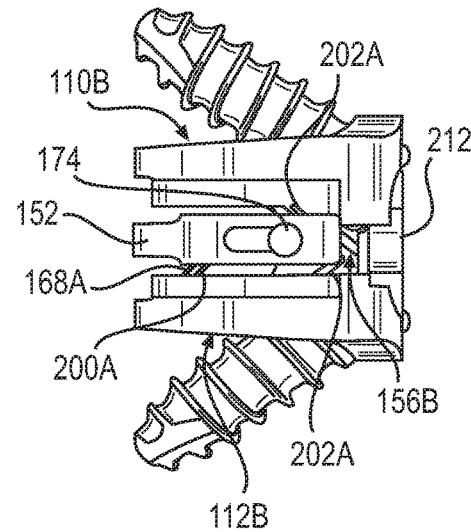
FIG. 28 depicts the implant of FIG. 24, with bone screws inserted into the implant.
Figure 29:
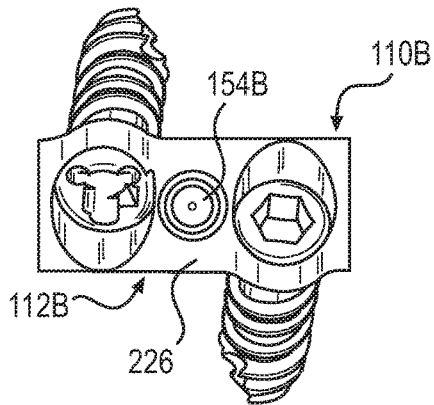
FIG. 29 depicts a front view of the implant of FIG. 27.
Figure 30:
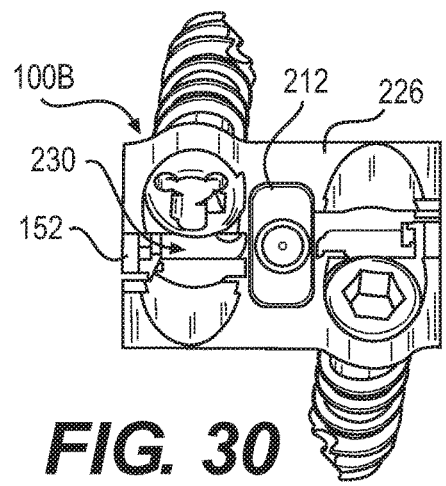
FIG. 30 depicts a front view of the implant of FIG. 28.
Figure 31:
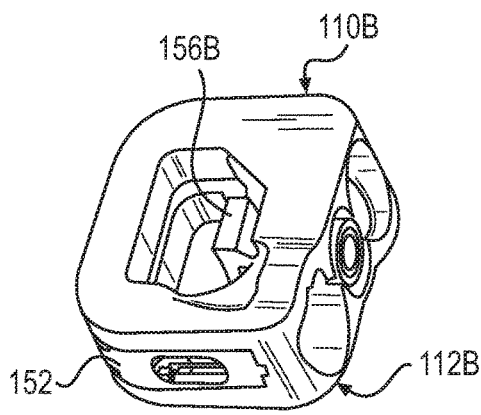
FIG. 31 depicts a perspective view of the implant of FIG. 19, without bone screws inserted.
Figure 32:
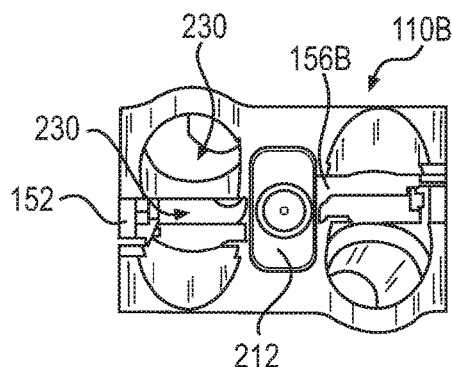
FIG. 32 depicts a front view of the implant of FIG. 30, without bone screws inserted.
Figure 33:
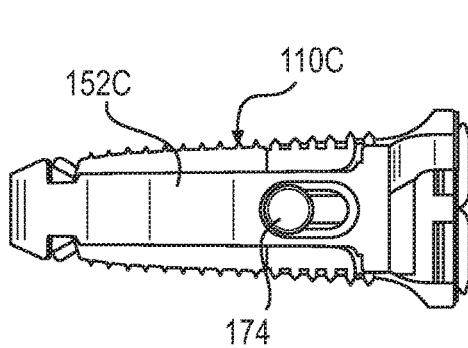
FIG. 33 depicts a side view of an alternative implant in accordance with the disclosure, in a reduced height configuration.
Figure 34:
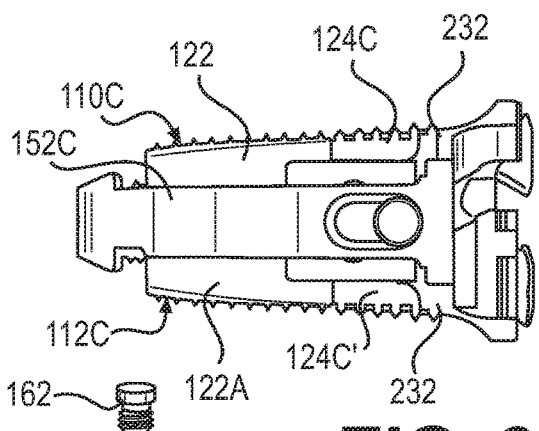
FIG. 34 depicts the implant of FIG. 33, in an expanded height configuration.

Step 7: Screw Insertion—In FIG. 17, bone screws 300 are inserted using bone screw driver 416. To facilitate access for bone screw driver 416, expansion driver 414 may be withdrawn from insertion tool 410. After bone screws 300 are inserted, they can be blocked from backing out using blocking element 120. Lagging of the vertebral bodies can be performed before or after the bone screws are locked. Fluoroscopy or other imaging can be used to confirm final placement. Imaging can also be used at any of the steps to confirm work performed. Further, bone screw hole preparation and bone screw 300 insertion can be carried out prior to implant 100 expansion, to promote anchoring of the implant during expansion. In FIG. 18, an expanded implant 100 can be seen between vertebrae, secured by bone screws 300. The foregoing method provides a customized fit using implant 100, and minimizes disruption to patient anatomy.

Referring now to FIGS. 19-32, an alternative implant 100B of the disclosure has a shorter actuator screw 154B relative to actuator screw 154 of implant 100 of FIG. 1. Actuator screw 154B engages a proximal end of carriage 156B, and does not pass through graft portal 208B. A compact actuator frame 212 includes a screw bearing 210, and upper and lower tabs 214, 216, respectively. Endplate slots 218, 220 within endplates 110B and 112B slidingly receive upper and lower tabs 214, 216. In this manner, actuator screw 154B is rotatably fixed along a longitudinal axis with respect to endplates 110B and 112B, the longitudinal axis indicated in FIG. 19 to extend between distal ("D") and proximal ("P") ends. Endplates 110B, 112B can slide upon collar tabs 214, 216 to mutually separate to form an expanded configuration of implant 100B. Actuator screw 154B can be rotatably retained within compact actuator frame 212, so that carriage 156B can be pushed or pulled in threaded engagement with actuator screw 154B, without an axial displacement of actuator screw 154B. This can be accomplished, for example, by a clip or other cooperative engagement between compact actuator frame 212 or bearing 210, and actuator screw 154B, or a blocking element (not shown) partially covering an end portion of actuator screw 154B. In an embodiment, tabs 214 and 216 form a dovetail connection with endplate slots 218, 220.

It should be understood that implant 100 may identified with a suffix herein, for example 100B, 100C, 100D, 100E, to indicate embodiments illustrating various features of the disclosure. In consideration of the impracticality of illustrating and describing every possible permutation of features, it should be understood that, where logical, features of the various implants may be substituted among the implants. Thus, all of the implants may collectively be referred to as implant 100, unless a specific reference is made to a feature illustrated by a particular embodiment.

Actuator screw 1546B threadably engages carriage 156B at threads 160B, whereby rotation of screw 154B causes carriage 156B to move towards or away from compact actuator frame 212. Carriage 156B has ramps 168, 168A and 170, 170A, which engage corresponding endplate ramps 164, 164A, 166, 166A as described with respect to implant 100. As actuator screw 154B is rotated, carriage 156 translates with respect to endplates 110B, 112B. As a result, carriage ramps 168, 168A and 170, 170A slide against endplate ramps 164, 164A, 166, 166A, causing endplates 110B, 112B to mutually separate. In an embodiment, carriage 156B is polymeric at threads 160B, and an interference fit is formed between actuator screw 154B and threads 160B, whereby sufficient friction is created to resist unintended rotation of actuator screw 154B, with a consequential change in height of implant 100B.

Frame 152 slidingly bears against frame support edges 224 extending along endplates 110B, 112B, and is slidingly connected to carriage 156B by carriage support screws 174. In this manner, carriage 156B is laterally supported, and inhibited from rotational movement, but may move longitudinally along a path defined by carriage support channel 176 and actuator screw 154B. Additionally, channels or dovetail guides 200, 202 in endplates 110B, 112B receive mating end portions 200A, 202A of carriage ramps 168, 168A, 170, 170A, to further guide and stabilize endplates 110B, 112B.

FIGS. 19-32 further illustrate an alternative blocking element 120B, which, as with other of the various alternative elements herein, may be combined with other implant embodiments herein. Element 120B forms an sliding block 226 within a block groove 228, block 226 and block groove 228 forming a dovetail or other sliding mating engagement, wherein block 226 is confined to movement along a path defined by block groove 228. Once bone screw head 302 is fully seated within bone screw socket 118, block 226 may be slid partially out of engagement with block groove 228 to a position over bone screw head 302, thereby blocking a movement of bone screw 300 out of engagement with body tissue. In the embodiment shown, two blocking elements 120B are illustrated, wherein a tool having two end portions (not shown) can be inserted adjacent each block 226, and the tool rotated to move both blocks into a blocking position. Accordingly, blocks 226 together form substantially concentric arcs pivoting about the same or close axes.

Implant 100B is configured to facilitate the insertion of graft material or other therapeutic material through one or more of bone screw socket 118 into graft chamber 204 formed by openings within endplates 110B, 112B, and carriage 156B. After the material is inserted, bone screws 300 may then be inserted into socket 118 and fastened to body tissue as otherwise shown and described herein. A bone funnel 440 (FIG. 40) may be used to urge material into graft chamber 204. Alternatively, once implant 100B is expanded, materials may be inserted into an endplate gap 230 formed by a separation of endplates 110B, 112B, as may best be seen in FIGS. 30 and 32, which are cross-sections taken through compact actuator frame 212, and upper and lower tabs 214, 216.

It should be understood that endplates of the disclosure, in all embodiments, may be formed of a unitary material, as illustrated in FIGS. 19-32 for example, or multiple materials, as illustrated in FIGS. 1-6 for example. Accordingly, endplates 110B, 112B may be formed of multiple materials, for example titanium for a proximal, bone screw engaging portion, and UHMWPE for a distal, bone engaging portion. Further, endplates 110B, 112B may be provided with teeth or other projections, to positively engage body tissue and reduce a likelihood of undesired migration of implant 100B.

With reference to FIGS. 33-40, a spacer implant 100C includes frame 152C which forms a dovetail engagement with upper and lower endplates 110C, 112C. In this manner, endplates 110C, 112C are further stabilized throughout a range of expansion of implant 100C. As may be seen in FIG. 36, a cross section of endplate portion 124C illustrates frame support channel 232 of endplate portion 124C is shaped to slidingly retain frame extension guide 234 of frame 152C (also visible in FIGS. 44-45). It should be understood that an inverse configuration can be created, wherein a channel is formed in frame 152C and an extension is formed from endplate portion 124C. Similar channels and extensions can be formed on opposing sides of frame 152C, as illustrated, with a frame support channel 232 formed in lower endplate portion 124C', as well. In an embodiment, frame 152C can form an extended region 238 along all or part of the dovetail engagement area of frame support channel 232 and extension guide 234. For example, frame 152C can extend in superior and inferior directions to extend from near an outer surface of endplate 110C to near an outer surface of endplate 112C, or may extend over a lesser distance. Channel 232 and extension guide 234 are illustrated as transverse to an A-P or longitudinal axis of implant 100C. In an alternative embodiment, channel 232 and guide 234 are disposed at a non-transverse angle with respect to the longitudinal axis.

Figure 35:
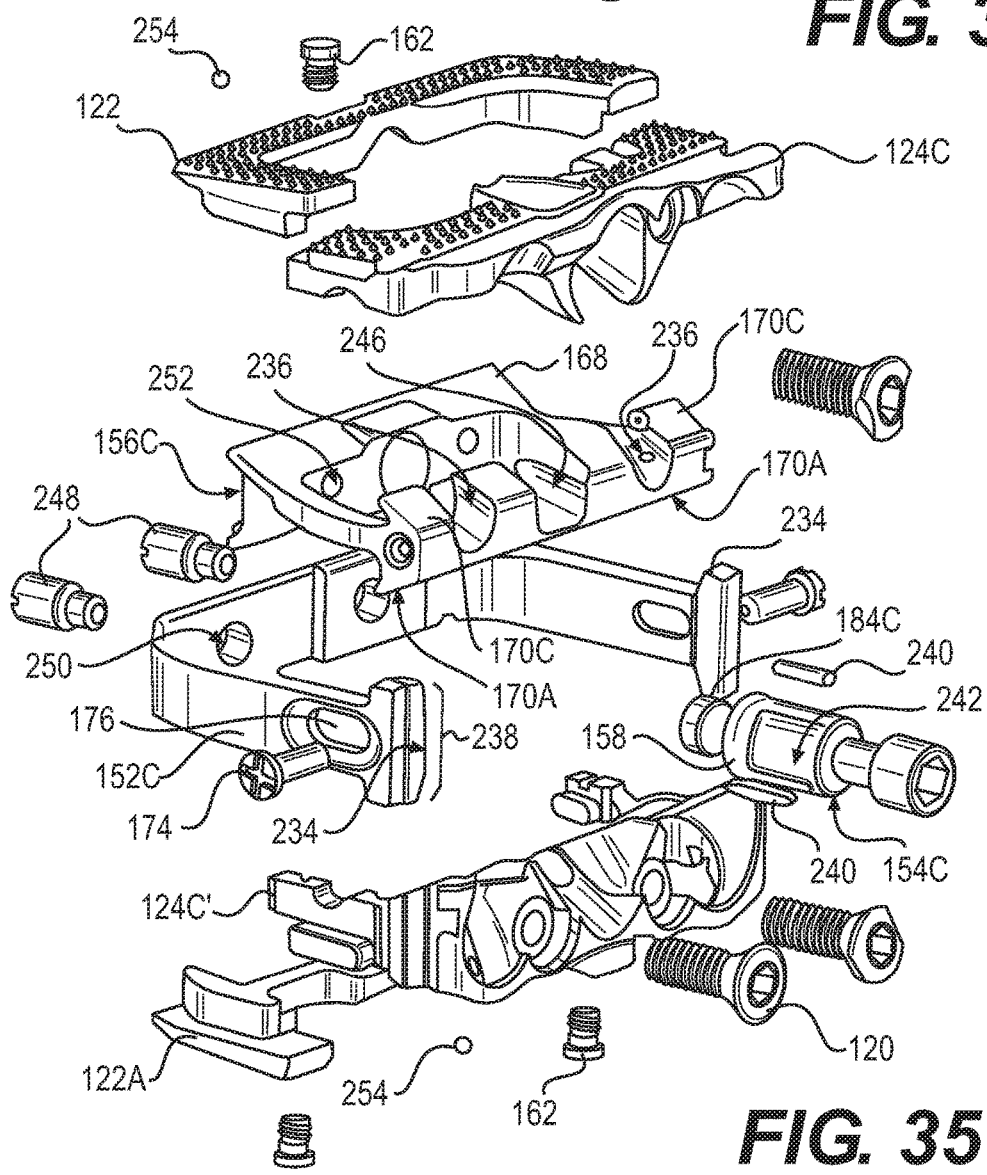
FIG. 35 depicts an exploded view of the implant of FIG. 33.
Figure 36:
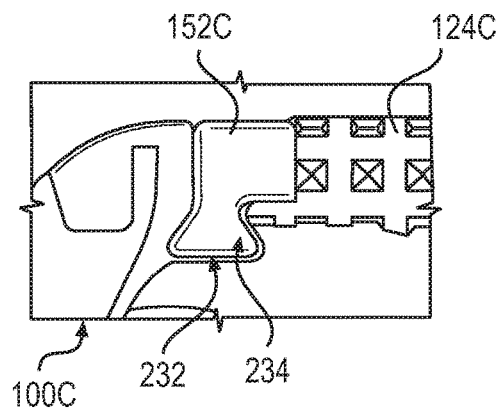
FIG. 36 depicts an enlarged cross section of a dovetail connection of the implant of FIG. 33.
Figure 37:
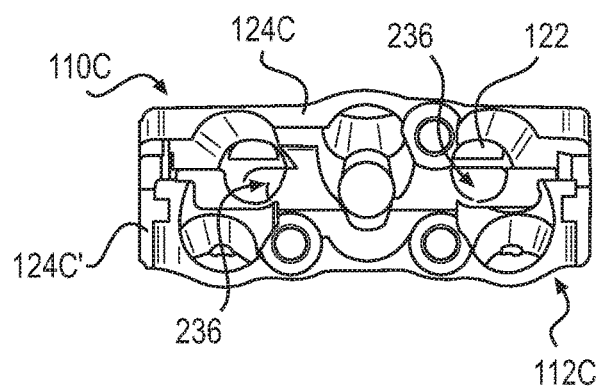
FIG. 37 depicts a front view of the implant of FIG. 33, illustrating passages for bone graft material.

With reference to FIGS. 35 and 37, carriage 156C includes a graft chamber portal 236, providing access from a exterior to a proximal end of implant 100C into graft chamber 204, after implant 100C is implanted within the body. Carriage 156C includes two portals 236 specifically formed to admit the passage of graft or other therapeutic materials, however one or more than two portals 236 can be provided. In the embodiment illustrated, graft chamber portals 236 are formed within a portion of carriage ramp 170, although other portions of carriage 156C may be shaped or opened in a like manner. A bone funnel 440 may be used to direct material through one or more of graft chamber portal 236.

Figure 38:
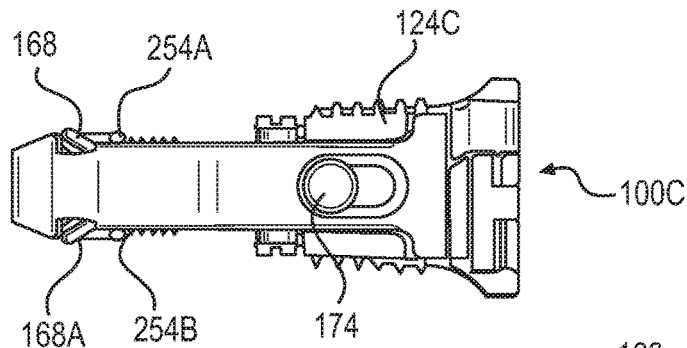
FIG. 38 depicts a simulating of radiographic imaging of an implant of the disclosure, illustrating radiographic markers, the implant in a reduced height configuration.
Figure 39:
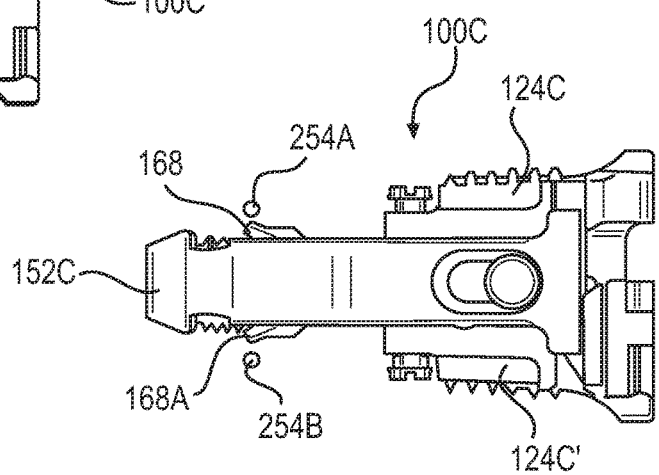
FIG. 39 depicts the implant of FIG. 38, the implant in an expanded height configuration.

As can be seen in FIG. 35, actuator screw 154C includes actuator screw bearing 184C and lateral screw bearings 240, provided to promote smooth rotation of actuator screw 154C. Bearing channels 242 within actuator screw 154C can be provided to maintain an orientation of lateral screw bearings 240 within screw guide 246 of carriage 156C. In an embodiment, an interference fit is formed between lateral screw bearings 240 and screw guide 246, to prevent unintended rotation of actuator screw 154C. To further stabilize carriage throughout at least a portion of its range of motion, stabilizing posts, screws, or pins 248 can be provided, connected to frame 152C, for example within frame pin bore 250 by threads, adhesive, or an interference fit, and slideably engageable within pin bores 252 within carriage 156C. Alternatively, pins 248 can be affixed to carriage 156C, and can slide within frame pin bores 152C. In an embodiment, As can be seen in FIGS. 35 and 38-39, one or more radiographic markers 254 are positioned within implant 100C, for example within radiotransparent portions of implant 100C, or any other radiotransparent portion of the various embodiments herein. For example, a radiographic marker can be positioned within polymeric endplate portion 122, 122A, so that an expanded or contracted position thereof may be positively ascertained using imaging. As may be seen in FIG. 39, radiographic markers 254A, 254B are oriented to be aligned with an end of carriage ramps 168, 168A, which in this embodiment are radiopaque, only when implant 100C is fully expanded. To indicate an extent of expansion, one or more radiopaque markers 254 can be positioned with respect to frame 152, carriage 156, or any other portion of implant 100 which does not move together with an endplate 110, 112, and which is radiopaque, or which is similarly configured with a radiopaque marker 254.

FIG. 40 illustrates a bone funnel 440 useable with implants 100, 100B, 100C, 100D, 100E (collectively, herein, 100) of the invention. An output aperture is placed proximate an opening into an open area within implant 100, for example graft chamber 204. Bone graft material, and or other therapeutic agents, are collected within including for example bone growth factors, antimicrobial agents, or other therapeutic is placed into widened input chamber 444, and then pushed down pipe 446 with a driver, for example a rod (not shown). A pipe connector 448 can be provided, sized to correspond to graft chamber portal 236. Driven bone graft material is passed into an interior of implant 100, where it may have its intended therapeutic benefit upon contacting body tissue of at least one vertebra.

In an embodiment, carriage ramps 168, 168A, 170, 170A can have differing ramp angles and or sizes, wherein endplate ramps 166, 166A have corresponding profiles and sizes. For example, if ramps 168, 168A are shorter than ramps 170, 170A, expansion will occur at a greater rate along a proximal side of implant 100, and in this manner an angular orientation of the spine, for example lordosis, may be corrected. Similarly, ramps 170, 170A can be shorter than ramps 168, 168A. Alternatively, one side of ramp 168, 168A can be shorter than another side of ramp 168, 168A, with a corresponding difference along ramps 170, 170A. In this manner, a sideways orientation of the spine, for example Scoliosis, may be corrected.

Figure 41:
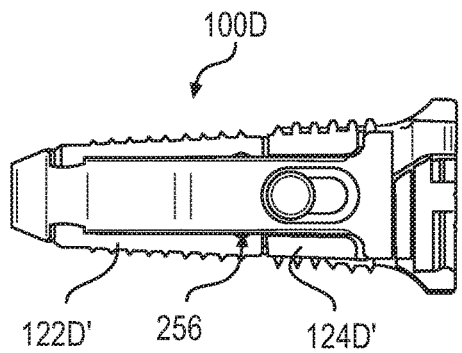
FIG. 41 depicts an alternative implant of the disclosure, including hinged endplates, in a reduced height configuration.
Figure 42:
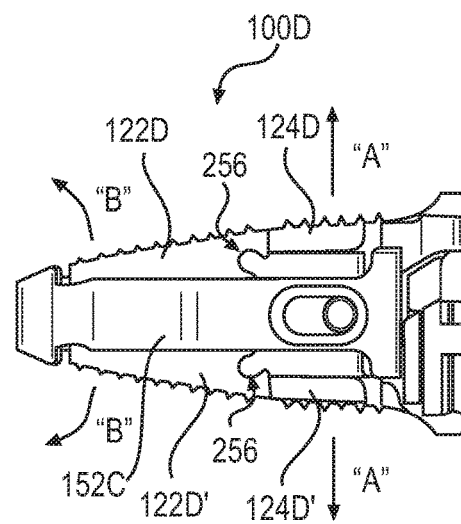
FIG. 42 depicts the implant of FIG. 41, in an expanded configuration.
Figure 43:
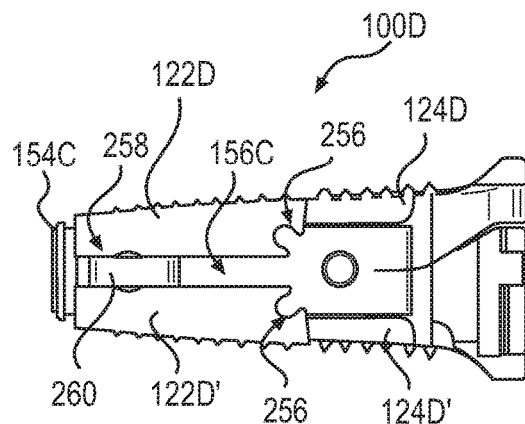
FIG. 43 depicts the implant of FIG. 41, with a frame portion removed.

FIGS. 41-43 illustrate an alternative implant 100D of the disclosure, which pivots proximate ends of endplates 110D, 112D, providing both axial translation, as indicated by arrows "A", and pivoting, as indicated by arrows "B". Axial translation is maintained using frame 152C, together with frame extension guide 234 and frame support channel 232, as described with respect to implant 100C. However, an endplate pivot 256 is formed between endplate portions 122D and 124D, and between endplate portions 122D' and 124D'. FIG. 43 illustrates implant 100D with frame 152C removed, illustrating a endplate hinge 258 formed between endplate portions 122D and 122D'. Connected in this manner, endplate portions 122D and 122D' pivot about endplate hinge 258, as well as endplate pivots 256. Accordingly, a height of implant 100D at a distal end of implant portions 122D and 122D' is held constant, while a proximate end of implant portions 122D and 122D' translates axially with endplate portions 124D and 124D' to increase a height of implant 100D.

Implant 100D can be inserted into the intervertebral disc space at a collapsed height, and then expanded into lordosis to restore sagittal balance and height loss in the disc space. Implant 100D provides distraction as well as achieving optimal sagittal balance. Further, implant 100D reduces impaction to body tissue during insertion at a collapsed height, and gives a medical practitioner the capability to continuously adjust the lordotic angle of the supporting endplates to best fit the patient's anatomy and therapeutic needs.

Endplate pivot 256 is formed as mating circular portions of endplate portions 122D and 124D, and of endplate portions 122D' and 124D'. While one endplate portions forms an extension, and the other a receptacle, it should be understood that this configuration may be reversed.

Endplate hinge 258 is formed as a flexible connector 260 extending between endplate portions 122D and 122D'. In an embodiment, endplate portions 122D and 122D' are molded as a single part from a polymeric or other flexible material, thus forming a living hinge. In a further embodiment, a hinge is formed between endplate portions 122D and 122D' by any known means, including a barrel or flag hinge, or a hinge similar in style to endplate pivots 256. In an alternative embodiment, endplate hinge 258 is formed in connection with frame 152C.

By providing both axial and pivoting movement of endplate portions, implant 100D enables the formation of an alternative supporting structure, and in particular, a supporting structure with a convex conformity. This can be useful to correct particular spinal problems, including lordosis, for example.

Figure 44:
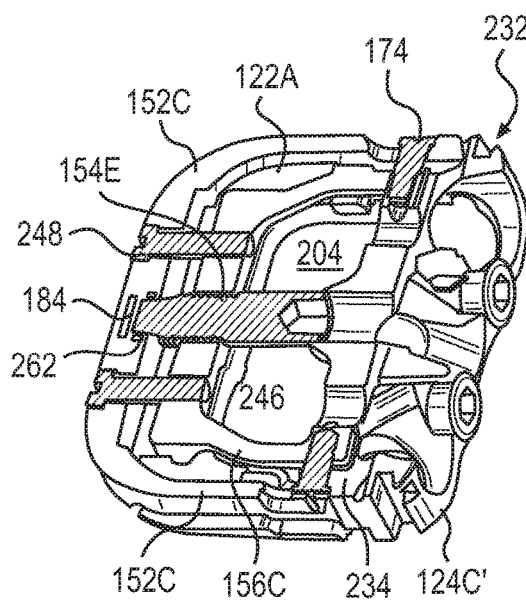
FIG. 44 depicts a cross section of an alternative implant of the disclosure, in perspective, having an elongate actuator screw.
Figure 45:
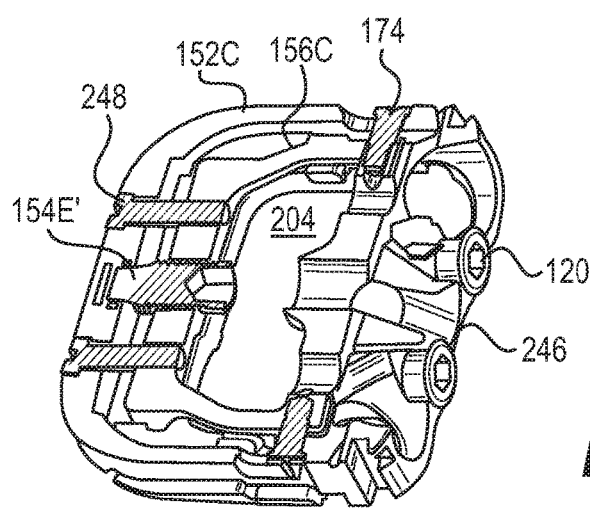
FIG. 45 depicts the implant of FIG. 44, having a shortened actuator screw.

With reference to FIGS. 44-45, which are cross-sections of an alternative implant 100E of the disclosure, it may be seen that actuator screw 154E is rotatably connected to frame 152E, for example using C-clip 262, as illustrated. An alternative method of rotatably securing actuator screw to frame 152E can include, for example, a leading set screw 178 (see, e.g. FIGS. 6, 6A) that freely spins relative to frame 152E, but is affixed to actuator screw 154E. An alternative method includes forming mating portions (not shown) upon frame 152E and screw 154E.

Further stability can be provided for carriage 156C through the use of stabilizing pins 248, frame pin bores 250, and pin bores in carriage 152C, as described with respect to implant 100C herein.

In a further embodiment, actuator screw 154E' is shorter than actuator screw 154E, and thereby reduces an obstruction of graft chamber 204. A tool can be passed through screw guide 246, and then through graft chamber 204, to engage actuator screw proximal end 182. Graft material can additionally be passed through screw guide 246, and placed within graft chamber 204. Bone funnel 140 can be used to pass materials through screw guide 246, and pipe connector can be adapted or replaced to best fit the dimensions of screw guide 246.

FIGS. 46-53 illustrate yet another embodiment according the present invention. Specifically, an intervertebral implant 300 for positioning between adjacent vertebral bodies is illustrated.

The purpose of the implant 300 is to insert it into the intervertebral disc space at a collapsed height, and then expand it axially to restore height loss in the disc space. The implant 300 would provide distraction as well as achieving optimal height restoration. This invention solves the problems currently encountered that include excessive impaction during insertion and visual obstruction and over distraction using a ramped inserter.

Figure 53:
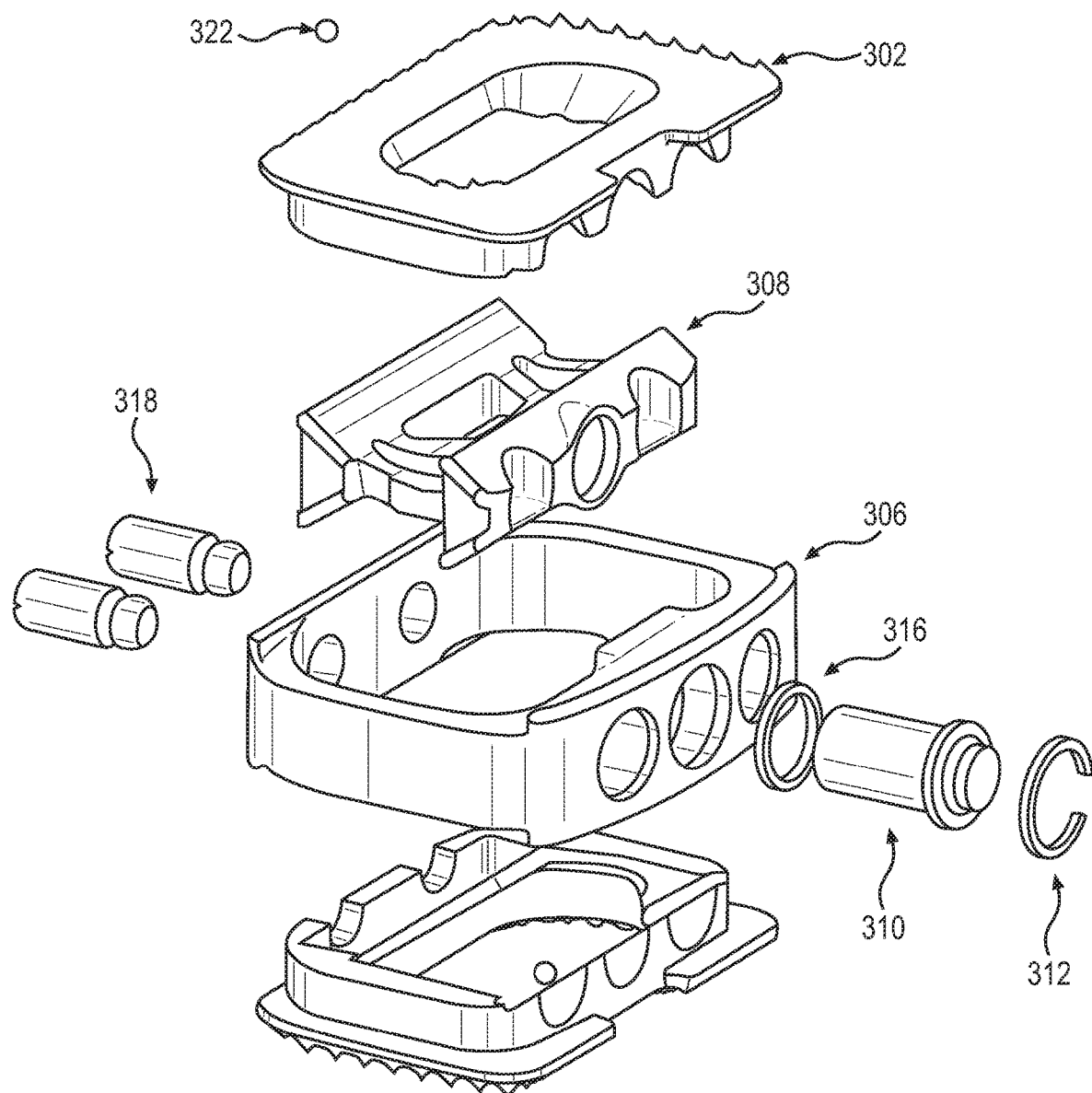

Turning to FIG. 53, an exploded view of the features of the implant are illustrated. The implant 300 comprises primarily a first endplate 302, a second endplate 304, a body 306, an actuator 308, and an actuator screw 310. The actuator 308 is configured so that it may translate relative to a body 306 by means of the threaded actuator screw 310. However, it any other type of actuator mechanism may be used such as a ratcheting system. The actuator 308 may have a larger, single axial opening for graft material, or have webbing for additional strength. The actuator screw 310 is fastened to the body using a retention clip 312, set screw, or other similar mechanical devices. The actuator 308 is also configured with ramped surfaces 314 that mate with ramped features on the first and second endplates 302, 304.

In operation, as the actuator 308 is linear translated, the actuator 308 causes the endplates to move axially to expand the implant, as illustrated in FIGS. 49-52. The actuator 308 is provided with dovetail features which enable the actuator 308 to capture the first and second endplates 302, 304 when collapsing the implant 300. A bushing 316 is used between the threaded set screw 310 and body 306 to minimize friction during expansion. Stabilizer screws 318 or pins can be used to capture the assembly and provide additional stability by sliding through specific slots in the body 306 and threading into the actuator 308. Additional inserts or a square nut can also be used to provide additional friction on the set screw threads to prevent height loss under cyclic loading. Bores 320 on the front face of the implant are used for packing additional graft material into the graft chamber after expansion. It should be noted that an instrument such a holder may be configured to attach to these features, or attach to another part of the implant.

Figure 46:
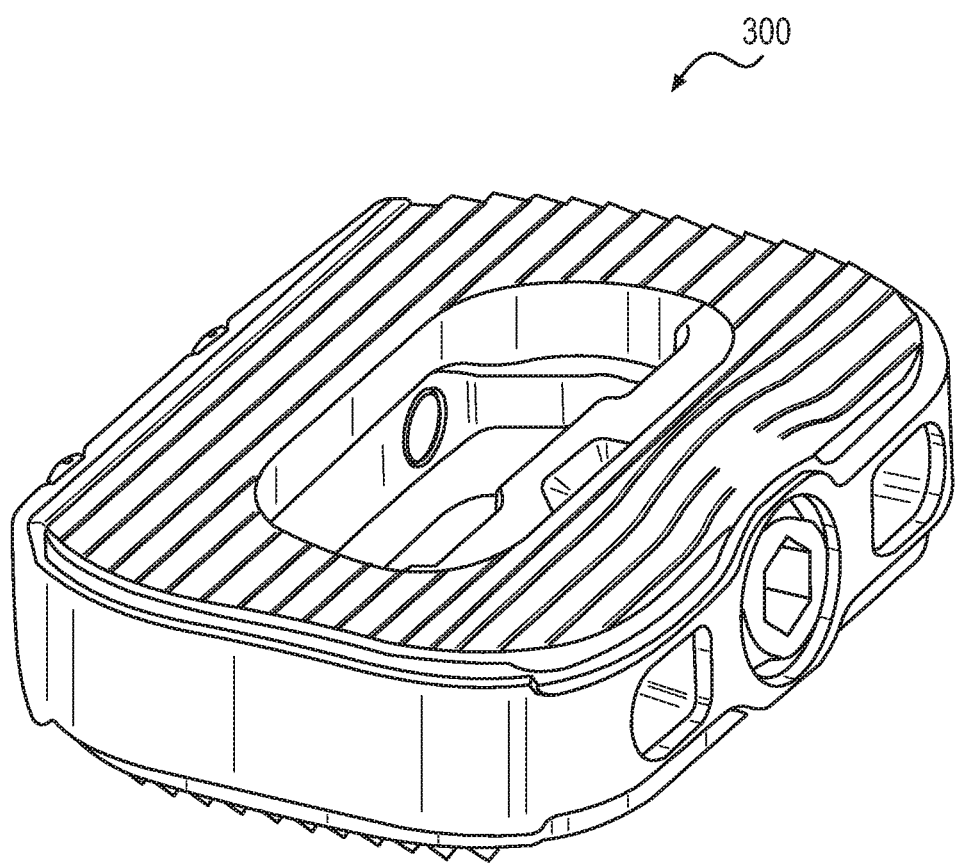
FIGS. 46-53 illustrate another embodiment of an implant according to the present invention.
Figure 47:
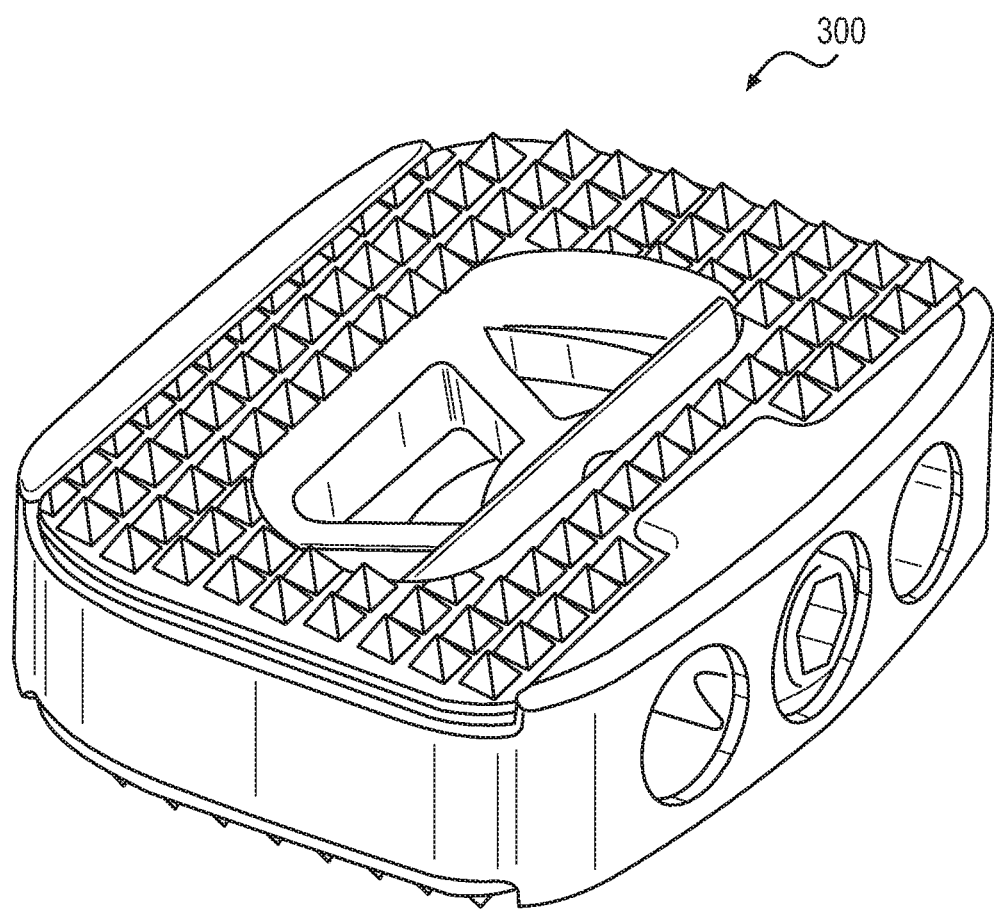
Figure 48:
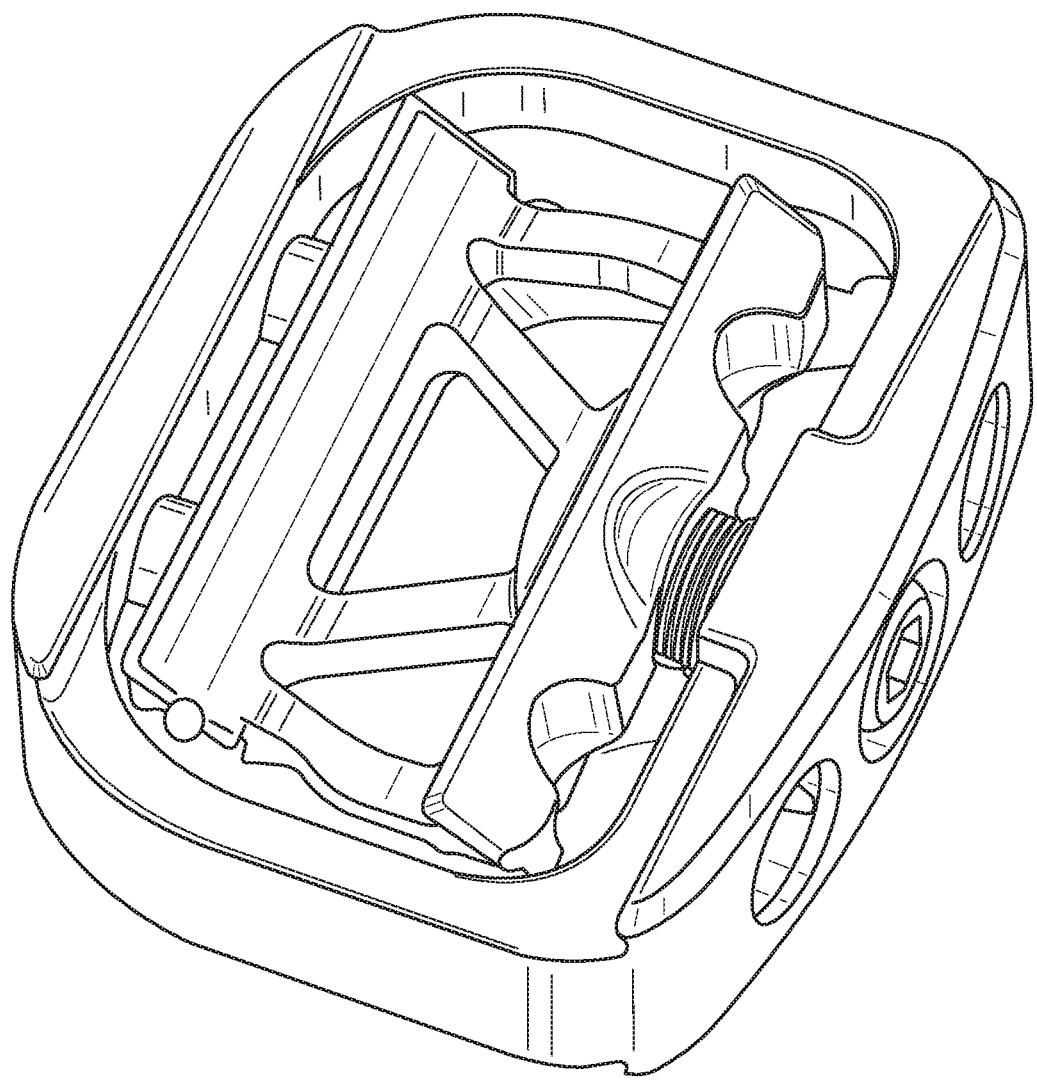
Figure 49:
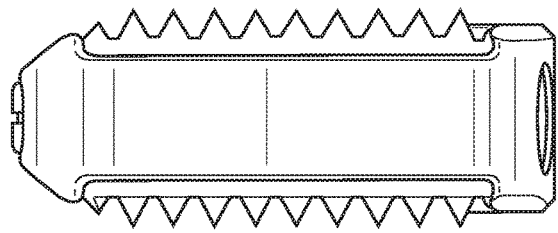
Figure 50:
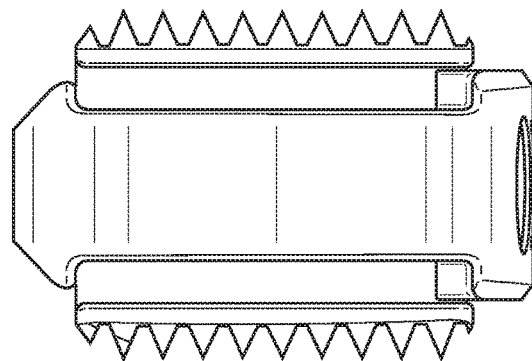
Figure 51:
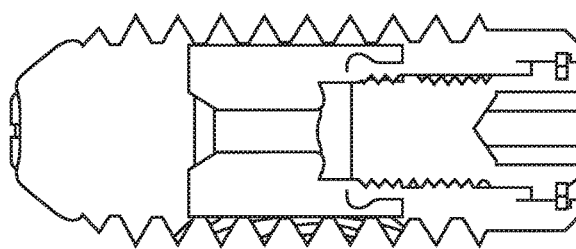
Figure 52:
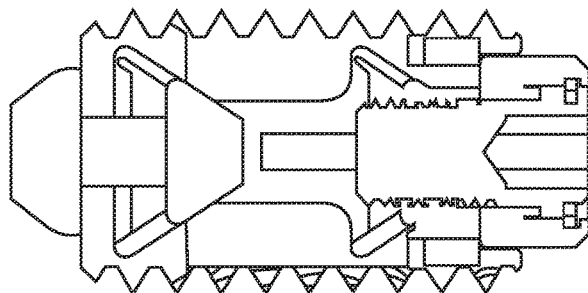

The first and second endplates are configured to cover the entire top surface as shown in FIG. 46 or a portion of it as shown in FIG. 47. The first and second endplates can have ridges or teeth to prevent post-operative cage migration. Radiopaque markers 322 can also be used to aid with fluoroscopic visualization. The assembly may also be provided with ports that provide access into the center graft chamber which can be used to pack additional graft material.

The advantage of this device is that it allows continuous expansion and distraction over the range of that specific implant. This provides the ability to distract vertebral bodies to a desired height, but also collapse the device for repositioning if desired. This implant has the ability for the endplates to converge providing lordosis and through windows cut for bone graft placement.

All references cited herein are expressly incorporated by reference in their entirety. There are many different features to the present invention and it is contemplated that these features may be used together or separately. Unless mention was made above to the contrary, it should be noted that all of the accompanying drawings are not to scale. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. An implant comprising:
a frame;
an actuator extending through the frame;
a carriage received within the frame, wherein the carriage is attached to the frame via a support element passable through a channel in the frame;
an upper endplate positioned above the frame, wherein the upper endplate includes at least one upper socket for receiving a bone screw therethrough; and
a lower endplate positioned below the frame, wherein the lower endplate includes at least one lower socket for receiving a bone screw therethrough,
wherein rotation of the actuator in a first direction causes the implant to move from an unexpanded configuration to an expanded configuration and rotation of the actuator in a second direction causes the implant to move from an expanded configuration to an unexpanded configuration,
wherein the carriage is slidable with respect to the frame, and
wherein the carriage includes at least one upper ramped surface and at least one lower ramped surface.

2. The implant of claim 1, wherein rotation of the actuator causes the at least one upper ramped surface to engage at least one ramp extending from the upper endplate and the at least one lower ramped surface to engage at least one ramp extending from the lower endplate, thereby causing the implant to move from the unexpanded configuration to the expanded configuration.

3. The implant of claim 1, wherein the upper endplate and the lower endplate are formed of metal.

4. The implant of claim 1, wherein the upper endplate includes one upper socket and the lower endplate includes two lower sockets.

5. The implant of claim 4, wherein a blocking element is associated with each socket for preventing a bone screw from backing out.

6. The implant of claim 5, wherein each of the blocking elements is rotatable.

7. An implant comprising:
a frame;
an actuator extending through the frame;
a carriage received within the frame, the carriage slideable with respect to the frame, wherein the carriage is attached to the frame via a support element passable through a channel in the frame;
an upper endplate positioned above the frame, wherein the upper endplate includes at least one upper socket for receiving a bone screw therethrough; and
a lower endplate positioned below the frame, wherein the lower endplate includes at least one lower socket for receiving a bone screw therethrough,
wherein rotation of the actuator causes the implant to move from an unexpanded configuration to an expanded configuration, and
wherein the carriage includes at least one upper ramped surface and at least one lower ramped surface.

8. The implant of claim 7, wherein the implant is sized and configured for insertion via an anterior approach.

9. The implant of claim 7, wherein the upper endplate and the lower endplate are non-parallel to one another.

10. The implant of claim 7, wherein the actuator extends through the carriage.

11. The implant of claim 10, wherein rotation of the actuator causes the carriage to translate.

12. The implant of claim 11, wherein translation of the carriage causes the upper endplate to move from the unexpanded configuration to the expanded configuration.

13. The implant of claim 7, wherein the lower endplate includes at least two lower sockets for receiving bone screws therethrough.

14. The implant of claim 13, further comprising a blocking fastener associated with each of the two lower sockets for preventing back out of bone screws.

15. A method of installing an implant comprising:
positioning an implant in an intervertebral space, the implant comprising:
a frame;
a translatable carriage attached to the frame via a support element passable through a channel in the frame;
an actuator extending through the carriage;
an upper endplate positioned above the carriage, wherein the upper endplate includes at least one upper socket for receiving a bone screw therethrough; and
a lower endplate positioned below the carriage, wherein the lower endplate includes at least one lower socket for receiving a bone screw therethrough,
wherein the carriage includes at least one upper ramped surface and at least one lower ramped surface,
rotating the actuator to cause the implant to move from an unexpanded configuration to an expanded configuration;
installing a first screw in the upper socket such that the first screw engages an upper vertebra;
installing a second screw in the lower socket such that the second screw engages a lower vertebra; and
placing graft material at least between the upper endplate and the lower endplate.

16. The method of claim 15, wherein the actuator comprises a rotatable screw, wherein rotation of the actuator causes translation of the translatable carriage.

17. The method of claim 16, wherein translation of the carriage causes the implant to move from the unexpanded configuration to the expanded configuration.

18. The method of claim 15, wherein the upper endplate is formed of titanium and the lower endplate is formed of titanium.

\* \* \* \* \*